US011769969B2

(12) United States Patent
Shah et al.

(10) Patent No.: US 11,769,969 B2
(45) Date of Patent: Sep. 26, 2023

(54) HYBRID ELECTRICAL CONNECTOR FOR HIGH-FREQUENCY SIGNALS

(71) Applicant: Samtec, Inc., New Albany, IN (US)

(72) Inventors: Jignesh H. Shah, New Albany, IN (US); Jean Karlo Williams Barnet, New Albany, IN (US)

(73) Assignee: SAMTEC, INC., New Albany, IN (US)

( * ) Notice: Subject to any disclaimer, the term of this patent is extended or adjusted under 35 U.S.C. 154(b) by 0 days.

(21) Appl. No.: 17/265,845

(22) PCT Filed: Oct. 24, 2019

(86) PCT No.: PCT/US2019/057826

§ 371 (c)(1),
(2) Date: Feb. 4, 2021

(87) PCT Pub. No.: WO2020/086823

PCT Pub. Date: Apr. 30, 2020

(65) Prior Publication Data

US 2021/0257785 A1 Aug. 19, 2021

Related U.S. Application Data

(60) Provisional application No. 62/704,026, filed on Oct. 25, 2018.

(51) Int. Cl.
*H01R 13/646* (2011.01)
*H01R 13/6474* (2011.01)
(Continued)

(52) U.S. Cl.
CPC ......... *H01R 13/6474* (2013.01); *H01R 12/72* (2013.01); *H01R 13/6581* (2013.01)

(58) Field of Classification Search
CPC ............ H01R 13/6474; H01R 13/6581; H01R 13/6473; H01R 13/646; H01R 13/658;
(Continued)

(56) References Cited

U.S. PATENT DOCUMENTS 4,674,812 A * 6/1987 Thom .................. H05K 7/1445 439/78
4,686,607 A * 8/1987 Johnson ............... H01R 12/716 361/791
(Continued)

FOREIGN PATENT DOCUMENTS

CN 201285941 Y 8/2009
CN 107039855 A 8/2017
(Continued)

OTHER PUBLICATIONS

Official Communication issued in International Patent Application No. PCT/US2019/057826, dated Feb. 20, 2020.
(Continued)

*Primary Examiner* — Harshad C Patel
(74) *Attorney, Agent, or Firm* — KEATING & BENNETT, LLP

(57) ABSTRACT

A connector includes a housing; a cage surrounding the housing; first contacts that are located in the housing and that transmit high-speed signals; second contacts that are located in the housing, that transmit low-speed signals, and that each include a portion that extends from a top surface of the housing; first cables connected to the first contacts; and second cables connected to the second contacts.

29 Claims, 23 Drawing Sheets

(51) Int. Cl.
*H01R 12/72* (2011.01)
*H01R 13/6581* (2011.01)

(58) Field of Classification Search
CPC .... H01R 13/648; H01R 12/72; H01R 12/712; H01R 12/71
USPC .......................................................... 439/83
See application file for complete search history.

(56) References Cited

U.S. PATENT DOCUMENTS

| | | | | |
|---|---|---|---|---|
| 5,282,112 | A * | 1/1994 | Bremer | H05K 3/222 361/788 |
| 5,429,521 | A * | 7/1995 | Morlion | H01R 12/712 439/607.06 |
| 5,926,378 | A * | 7/1999 | DeWitt | H05K 1/14 710/301 |
| 5,931,686 | A * | 8/1999 | Sasaki | H01R 12/716 439/78 |
| 6,077,122 | A * | 6/2000 | Elkhatib | H01R 13/5837 439/417 |
| 6,392,142 | B1 * | 5/2002 | Uzuka | H05K 7/1445 174/541 |
| 6,932,640 | B1 | 8/2005 | Sung | |
| 7,249,966 | B2 * | 7/2007 | Long | H01R 13/6587 439/490 |
| 7,463,495 | B2 * | 12/2008 | Tanaka | H05K 7/20418 361/752 |
| 7,500,871 | B2 * | 3/2009 | Minich | H01R 12/727 439/544 |
| 7,520,774 | B2 | 4/2009 | Watanabe | |
| 7,540,744 | B1 * | 6/2009 | Minich | H05K 1/18 439/65 |
| 7,544,096 | B2 * | 6/2009 | Cohen | H05K 7/1445 439/607.05 |
| 7,666,009 | B2 * | 2/2010 | Minich | H01R 13/6587 439/101 |
| 7,677,900 | B2 | 3/2010 | Crighton | |
| 8,251,745 | B2 * | 8/2012 | Johnescu | H01R 12/71 439/607.1 |
| 8,361,896 | B2 * | 1/2013 | De Geest | H05K 1/0231 438/607 |
| 8,535,069 | B2 * | 9/2013 | Zhang | H01R 13/6471 439/607.05 |
| 8,545,267 | B2 * | 10/2013 | Fogg | H01R 13/6477 439/607.25 |
| 8,758,048 | B2 * | 6/2014 | Nesme | H04Q 1/14 439/94 |
| 8,944,830 | B2 | 2/2015 | Little et al. | |
| 8,968,031 | B2 * | 3/2015 | Simmel | H01R 13/6594 439/108 |
| 9,252,538 | B2 * | 2/2016 | Recce | H01R 13/641 |
| 9,325,086 | B2 * | 4/2016 | Brodsky | H01R 12/716 |
| 9,572,409 | B2 * | 2/2017 | Pidgeon | A61M 1/90 |
| 9,608,377 | B1 * | 3/2017 | Phillips | G02B 6/001 |
| 9,634,434 | B1 * | 4/2017 | Pao | H01R 13/6471 |
| 9,660,364 | B2 | 5/2017 | Wig et al. | |
| 9,748,681 | B1 | 8/2017 | Champion et al. | |
| 10,276,995 | B2 * | 4/2019 | Little | H01R 13/6273 |
| 10,530,081 | B1 | 1/2020 | Costello et al. | |
| 10,958,005 | B1 * | 3/2021 | Dube | H01R 12/737 |
| 2002/0025720 | A1 * | 2/2002 | Bright | H01R 13/6586 439/541.5 |
| 2003/0137817 | A1 | 7/2003 | Volstorf | |
| 2005/0095902 | A1 * | 5/2005 | Zhang | H01R 12/79 439/493 |
| 2005/0255726 | A1 | 11/2005 | Long | |
| 2006/0094292 | A1 | 5/2006 | Shindo | |
| 2009/0147493 | A1 * | 6/2009 | Wu | H05K 9/0016 361/818 |
| 2011/0053415 | A1 * | 3/2011 | Fonteneau | H05K 9/0058 361/816 |
| 2012/0135642 | A1 | 5/2012 | Chang | |
| 2013/0040492 | A1 * | 2/2013 | Wu | H01R 13/5808 439/607.55 |
| 2016/0218455 | A1 * | 7/2016 | Sayre | H01R 13/6594 |
| 2018/0034211 | A1 * | 2/2018 | Little | H01R 12/721 |
| 2018/0034492 | A1 * | 2/2018 | Edgren | H05K 7/20418 |
| 2018/0277973 | A1 * | 9/2018 | Regnier | H01R 13/6583 |
| 2018/0287314 | A1 | 10/2018 | Rothermel | |

FOREIGN PATENT DOCUMENTS

| | | | |
|---|---|---|---|
| TW | 201710724 | A | 3/2017 |
| TW | 201724660 | A | 7/2017 |
| TW | 201813214 | A | 4/2018 |
| TW | M593670 | U | 4/2020 |
| WO | 2020/086823 | A1 | 4/2020 |

OTHER PUBLICATIONS

Official Communication issued in corresponding Taiwanese Patent Application No. 108138583 dated Nov. 9, 2020.

Palkert et al., “QSFP Double Density 8X Pluggable Transceiver,” Rev. 3.0, Sep. 19, 2017, pp. 1-69.

Palkert et al., “QSFP Double Density 8X Pluggable Transceiver,” Rev. 4.0, Sep. 19, 2018, pp. 1-68.

Official Communication issued in corresponding Taiwanese Patent Application No. 108138583 dated Jun. 10, 2020.

Wig et al., “Method, Apparatus, System for a High-Speed Digital Interconnect Scheme Using Directly Attached Cablin,” U.S. Appl. No. 61/714,871, filed Oct. 17, 2012.

TE Connectivity, “Featured Product: zQSFP+ Cages & Connector for Intel Omni-Path Architecture, Excellent I/O electrical performance and high density for use in Intel Omni-Path Architecture (OPA)”, https://www.te.com/usa-en/about-te/news-center/zqsfp-plus-belly-to-belly.html, Sep. 27, 2017, 4 pages.

* cited by examiner

METHOD OF ASSEMBLY FOR AN INTEGRATED PCB ASSEMBLY

HYBRID ELECTRICAL CONNECTOR FOR HIGH-FREQUENCY SIGNALS

BACKGROUND OF THE INVENTION

1. Field of the Invention

The present invention relates to electrical connectors. More specifically, the present invention relates to hybrid high-frequency electrical connectors that include connections to cables and to a substrate or circuit board.

2. Description of the Related Art

Electrical connectors are used to allow electrical devices, such as substrates or printed circuit boards (PCBs), to communicate with one another. Electrical connectors are also used along the path between electrical devices to connect cables to other cables or to PCBs. A connector may be thought of as having two portions, a first portion which connects to a first electrical device or a first cable and a second portion which connects to a second electrical device or a second cable, to be put into communication with the first device or first cable. To connect the two electrical devices or cables, the first and second portions of the connector are mated together.

A connector can include a first set of contacts in the first portion and a second set of contacts in the second portion to be connected with the contacts of the first portion. This can be readily accomplished by providing a male connector and a female connector with corresponding sets of contacts that engage when the male and female connectors are mated. Further, the male and female connectors can be connected and disconnected from each other to respectively electrically connect and disconnect the electrical devices to which they are connected.

Accordingly, the first and second connector portions are connected to an electrical device or cable through its contacts. The contacts are typically permanently connected to the electrical device or cable. For example, the first connector portion can be connected to a cable, and the second connector portion can be connected to a PCB. The first connector portion can be connected to the second connector portion to allow transmission of signals to and from devices on and/or in the PCB. The second connector portion is connected to devices on and/or in the PCB via electrical traces etched in the PCB.

Various standards and specifications have been proposed and implemented for electrical connectors that transmit high-frequency signals. One example is Quad Small Form-factor Pluggable (QSFP/QSFP+), which is a specification for compact, hot-pluggable transceivers typically used in data communication systems. FIG. 1 is a perspective view of a conventional QSFP/QSFP+ type of connector disclosed in U.S. Patent Application No. 2016/0218455, which is limited to a data transfer rate of about 10 Gbit/sec per channel (about 40 Gbit/sec total).

As shown in FIG. 1, a mating cable 4 is connected to a male QSFP connector 1, which mates with a female QSFP connector 2A included in a cage 2 mounted to a PCB 5. The male QSFP connector 1 includes a housing 1A and a circuit board 10. The cage 2 of the female QSFP connector 2A includes a heat sink 3. Input signals from the mating cable 4 are transmitted between the connectors 1 and 2A and then transmitted to the PCB 5. The signals are then transmitted through electrical traces (not shown) in or on the PCB 5. For example, the signals may be transmitted through the electrical traces in the PCB 5 to an integrated circuit (IC) or other electrical components. However, this arrangement results in a bottleneck for data transmission due to the female QSFP connector 2A being terminated to the PCB 5.

FIG. 2 is a graph comparing the signal insertion loss through a cable and the signal insertion loss through traces on a PCB 5. As shown in FIG. 2, even a "low loss" etching for an electrical trace in a PCB has a significantly greater signal insertion loss as compared with an equivalent length of #28 AWG (American wire gauge) cable, especially at higher frequencies. For example, at a frequency of 20 GHz, there is an approximately 36 dB difference in the signal insertion loss for transmission through a cable as compared with transmission through an electrical trace in a PCB.

Thus, whereas the cable provides a signal path with high signal integrity (for example, an optical cable or shielded cable, such as a coaxial cable or twinaxial cable), the electrical traces in the PCB provide a signal path with a lower signal integrity, especially at higher frequencies. In particular, electrical traces in the PCB have much higher differential signal insertion loss than an optical or shielded cable and are far more susceptible to interference and cross-talk, even if components, such as ICs, are arranged on the PCB close to the female QSFP connector 2A.

FIG. 3 shows a plan view of a substrate 14 comparing the footprint of a known multi-source agreement (MSA) QSFP-DD compliant connector. As shown in FIG. 3, the footprint includes an array of lands 16 that the receptacle body of the known MSA QSFP-DD compliant connector can be mounted to and includes press-fit holes 18 that the press-fit tails of the cage and of the receptacle body of the known MSA QSFP-DD compliant connector can be inserted into.

SUMMARY OF THE INVENTION

To overcome the problems described above, an embodiment of the present invention provides an electrical connector connected to an auxiliary substrate that uses low-speed connections connected to electrical traces in the auxiliary substrate to transmit low-frequency signals, ground, and power, and that uses high-speed connections connected to cables to transmit high-frequency signals. In other words, a connector according to an embodiment of the present invention is a hybrid connector with cable connections that transmit high-frequency signals and board connections to transmit other signals.

One technical solution described herein is the fitting of a first electrical connector with a first mating interface, a first mounting interface and attached cables onto a substrate footprint configured to receive a second electrical connector with the first mating interface, a second mounting interface that is different from the first mounting interface, and no attached cables. For example, the first electrical connector can be a FQSFP-DD receptacle cable connector manufactured by SAMTEC, Inc., and the second electrical connector can be a QSFP-DD receptacle board connector. Stated another way, a first electrical connector can include a first mating interface, a first mounting interface, and N-number of electrical contacts to be modified to form a second electrical connector with the first mating interface, a second mounting interface that is different from the first mounting interface, and the same N-number of electrical contacts. The second mounting interface can correspond to a substrate footprint. Respective first mounting ends of a given number of N-number of electrical contacts each define the first mounting interface of a second electrical connector housing and respective second mounting ends of a given number of N-number of electrical contacts each extend from another side of the second electrical connector housing to accommodate attached cables. The other side of the second electrical connector housing, such as a top surface, can be positioned parallel to the first or second mounting interfaces, so that the respective second mounting ends correspond with, and do not interfere with, the substrate footprint. The substrate footprint can be the QSFP-DD board connector footprint, shown in FIG. 3.

According to an embodiment of the present invention, a connector includes a housing; a cage surrounding the housing; first contacts that are located in the housing and that transmit high-speed signals; second contacts that are located in the housing, that transmit low-speed signals, and that each include a portion that extends from a top surface of the housing; first cables connected to the first contacts; and second cables connected to the second contacts.

The connector can further include a control substrate, wherein the portion of each of the second contacts that extends from the top surface of the housing is connected to the control substrate, and the second cables are connected to the second contacts through the control substrate. The second cables can be crimped to the portion of each of the second contacts that extends from the top surface of the housing. The connector can further include wafers located within the housing, wherein the second contacts are included in the wafers. The connector can further include additional second contacts that are located in the housing, that transmit low-speed signals, that each include a portion that extends from a bottom surface of the housing, and that are not connected to any cables.

The connector can further include additional first contacts that are located in the housing and that are connected to ground. The first cables can include shields, and the additional first contacts can be connected to the shields. Each of the second contacts can include a right angle bend. The connector can be compatible with QSFP specifications.

According to an embodiment of the present invention, a connector system includes a base substrate and a connector according to one of the various other embodiments of the present invention connected to a first surface of the base substrate.

The connector system can further include an additional connector connected to a second surface of the base substrate opposite to the first surface, wherein the additional connector includes a housing and a cage surrounding the housing. The additional connector can be compatible with QSFP specifications.

According to an embodiment of the present invention, a stacked connector includes a first connector that includes first low-speed contacts and first high-speed contacts; a second connector that is stacked on top of the first connector and that includes second low-speed contacts and second high-speed contacts, wherein each of the second low-speed contacts includes a portion that extends from a top surface of the second connector; a cage surrounding the first connector and the second connector; first high-speed cables connected to the first high-speed contacts; second high-speed cables connected to the second high-speed contacts; and low-speed cables connected to the second low-speed contacts.

The stacked connector can further include a control substrate, wherein the portion of each of the second low-speed contacts that extends from the top surface of the second connector are connected to the control substrate, and the low-speed cables are connected to the second low-speed contacts through the control substrate. The low-speed cables can be crimped to the portion of each of the second low-speed contacts that extends from the top surface of the second connector.

The first connector can further include additional first low-speed contacts that each include a portion that extends from a bottom surface of the housing and that are not connected to any cables. The first low-speed contacts can be connected to the low-speed cables. The stacked connector can further include a spacer between the first connector and the second connector. The first connector and the second connector can be compatible with QSFP specifications.

According to an embodiment of the present invention, a stacked connector system includes a base substrate and a stacked connector system according to one of the various other embodiments of the present invention connected to the base substrate.

According to an embodiment of the present invention, a connector system includes a base substrate; a first connector connected to a first surface of the base substrate and including a first housing including first contacts directly connected to the base substrate in a first area and a first cage surrounding the first housing; and a second connector connected to a second surface of the base substrate opposite to the first surface and including a second housing including second contacts directly connected to the base substrate in a second area and a second cage surrounding the second housing. When viewed in a plan view with respect to the base substrate, the first and second areas do not overlap.

The first connector and the second connector can be compatible with QSFP specifications.

A connector can include a housing, a cage surrounding the housing, first contacts that are: (i) located in the housing, (ii) that transmit high-speed signals, (iii) that are configured to attach to a mounting substrate, and (iv) that define a mounting interface, second contacts that are: (i) located in the housing, (ii) that transmit low-speed signals, and (iii) that each include a portion that extends from a top surface of the housing, the top surface of the housing positioned parallel to the mounting interface, and second cables electrically connected to the second contacts.

The above and other features, elements, steps, configurations, characteristics and advantages of the present invention will become more apparent from the following detailed description of embodiments of the present invention with reference to the attached drawings.

DETAILED DESCRIPTION OF EMBODIMENTS

Embodiments of the present invention will now be described in detail with reference to FIGS. 4 to 32. Note that the following description is in all aspects illustrative and not restrictive, and should not be construed to restrict the applications or uses of the present invention in any manner.

Figure 1:
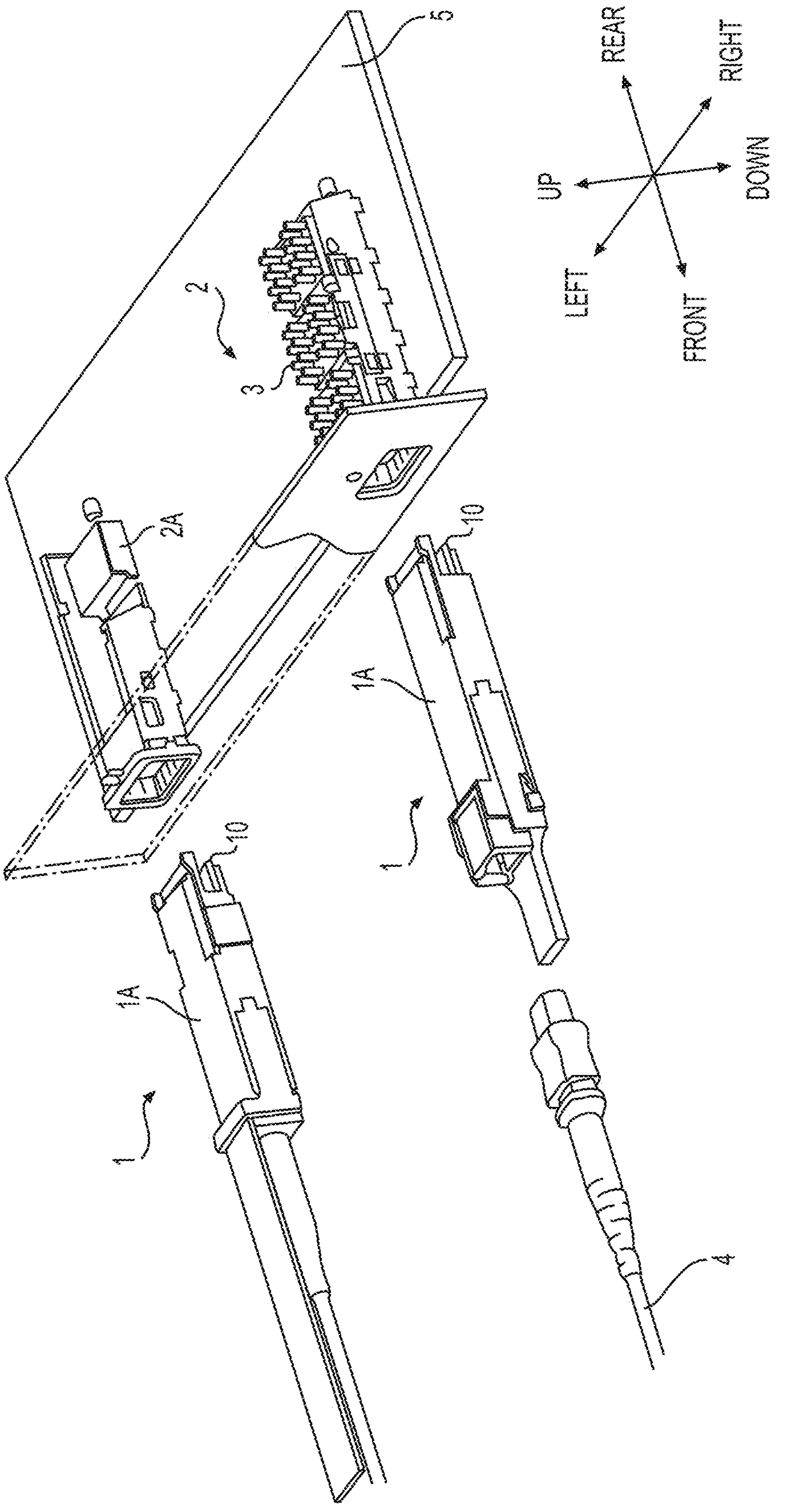
FIG. 1 (PRIOR ART)
FIG. 1 is a perspective view of a conventional QSFP connector.
Figure 2:
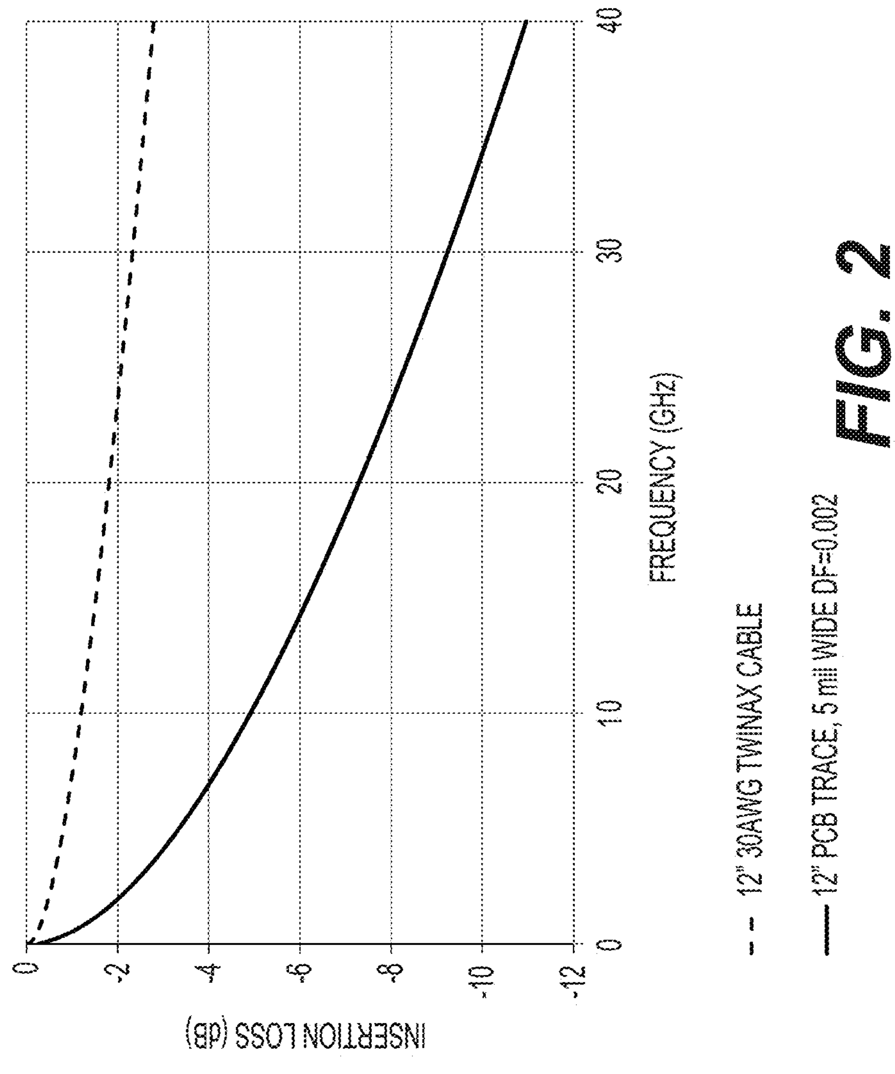
FIG. 2 (PRIOR ART)
FIG. 2 is a graph comparing the signal loss through a cable and the signal loss through traces on a printed circuit board (PCB).
Figure 3:
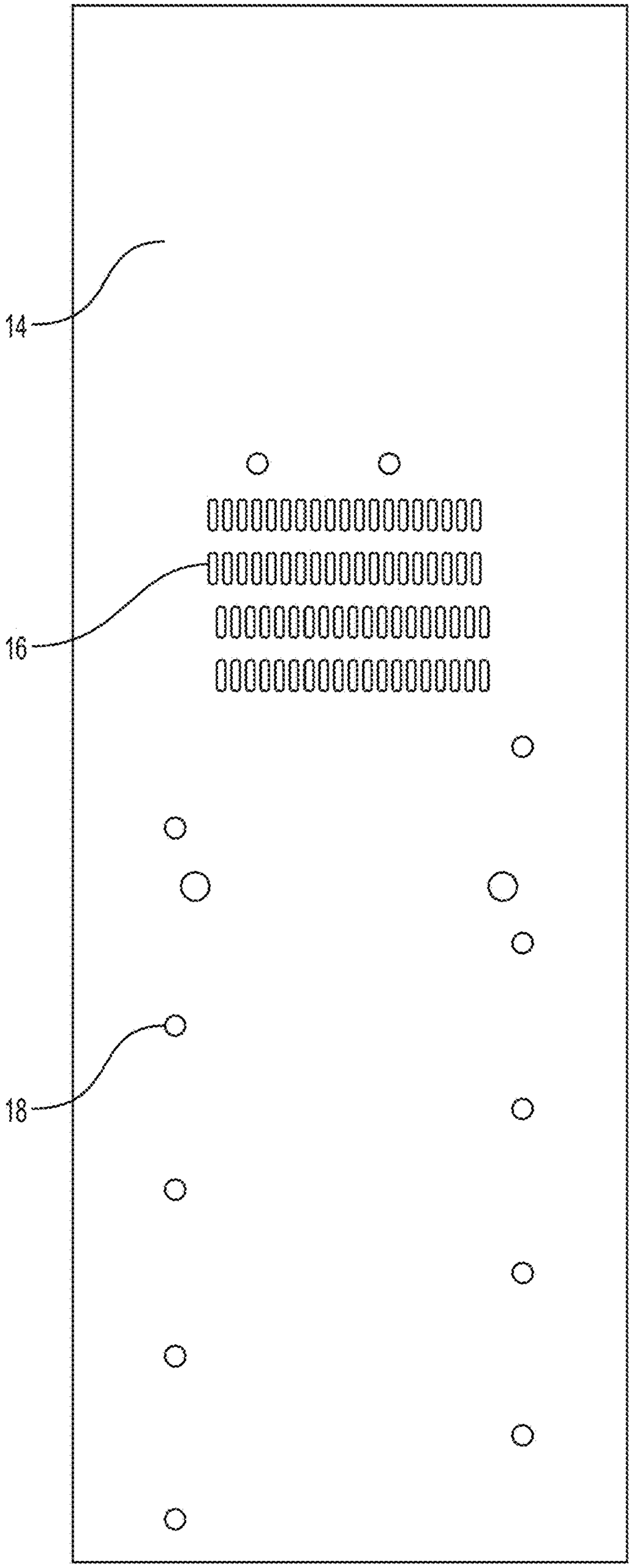
FIG. 3 (PRIOR ART)
FIG. 3 shows a plan view of a footprint of a known QSFP-DD connector.
Figure 4:
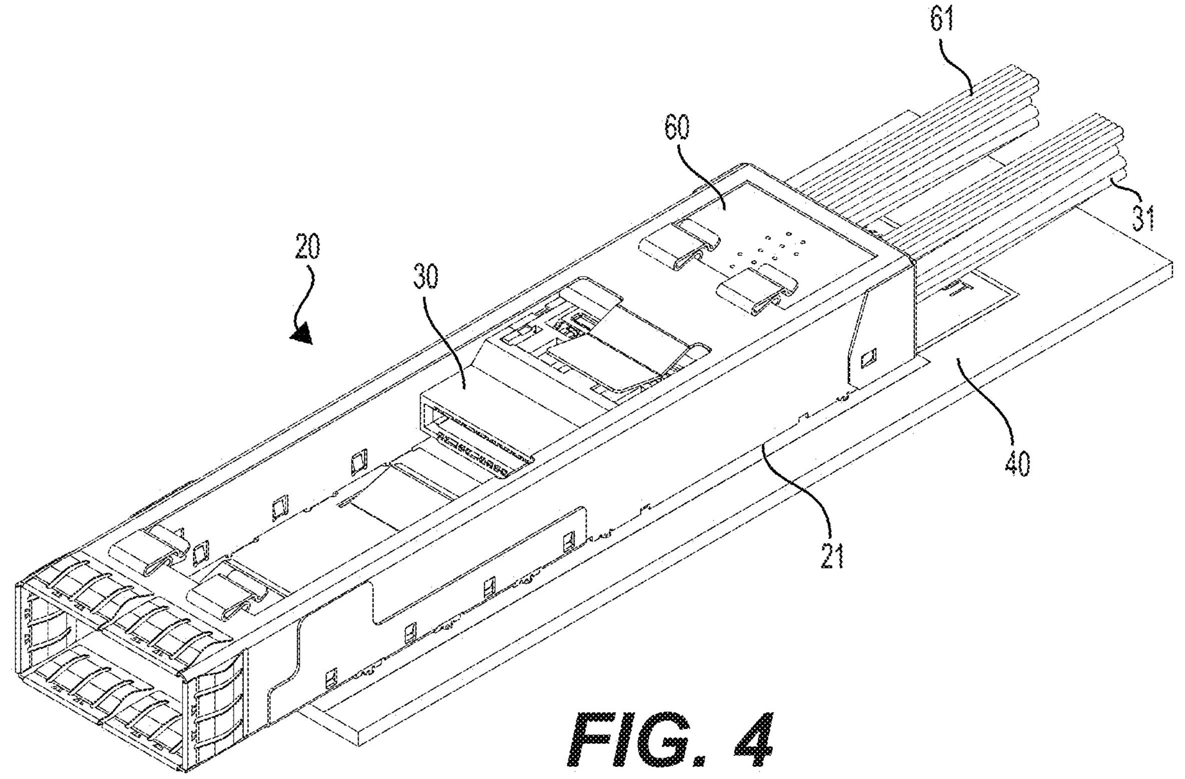
FIGS. 4 and 5 are front and rear perspective views of a connector according to a first embodiment of the present invention.
Figure 5:
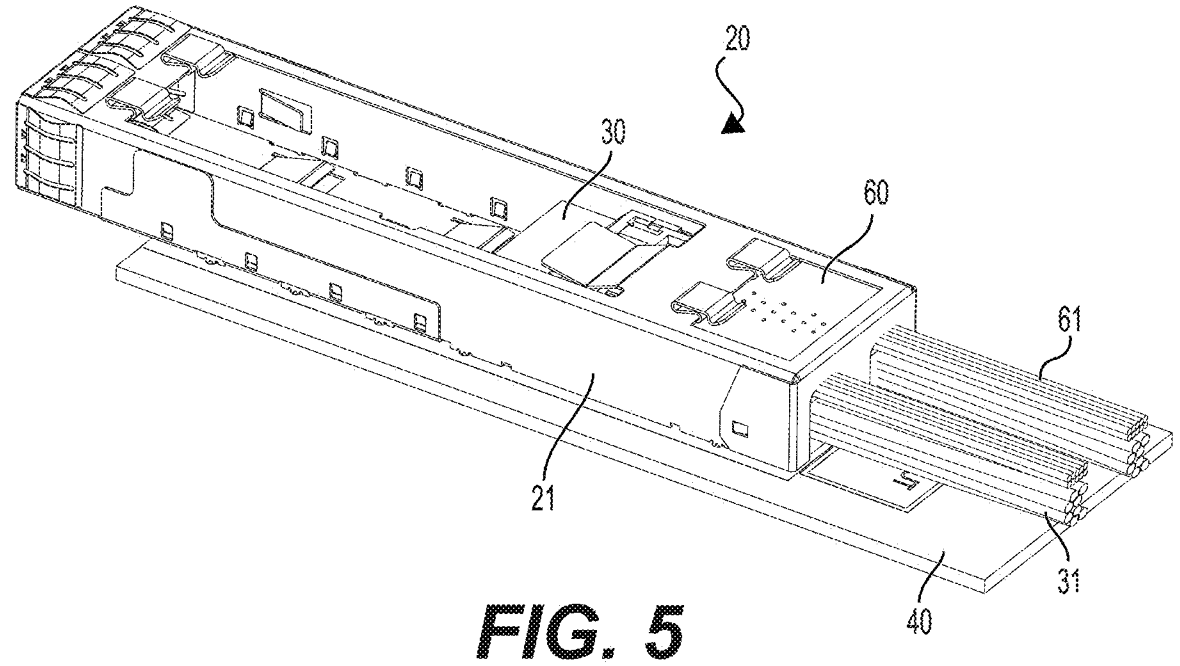
Figure 6:
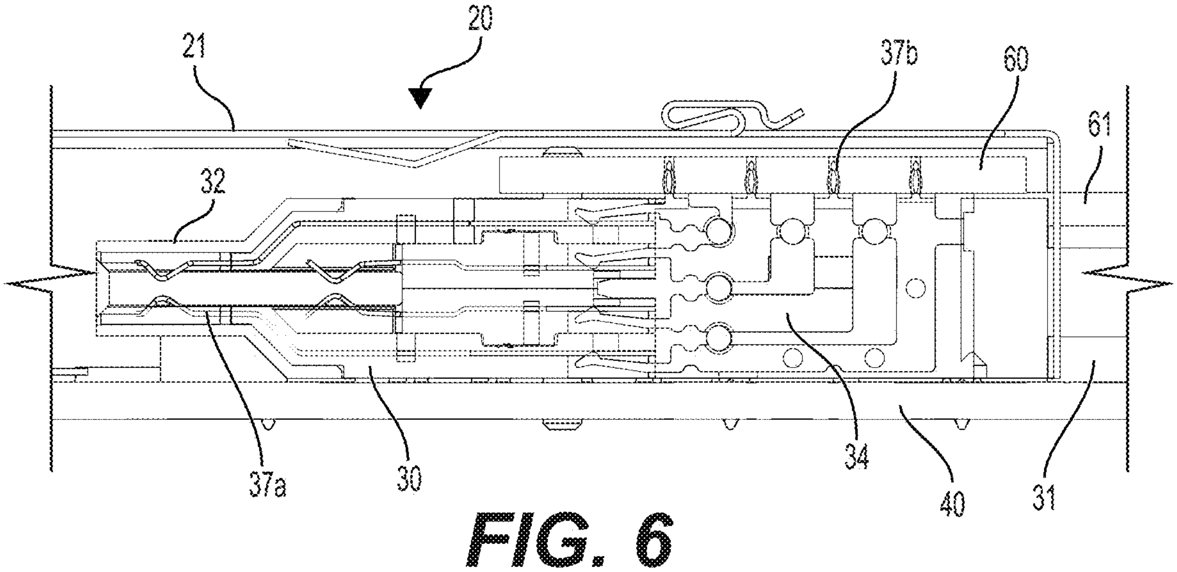
FIG. 6 is a cross-sectional view of the connector shown in FIGS. 4 and 5.
Figure 7:
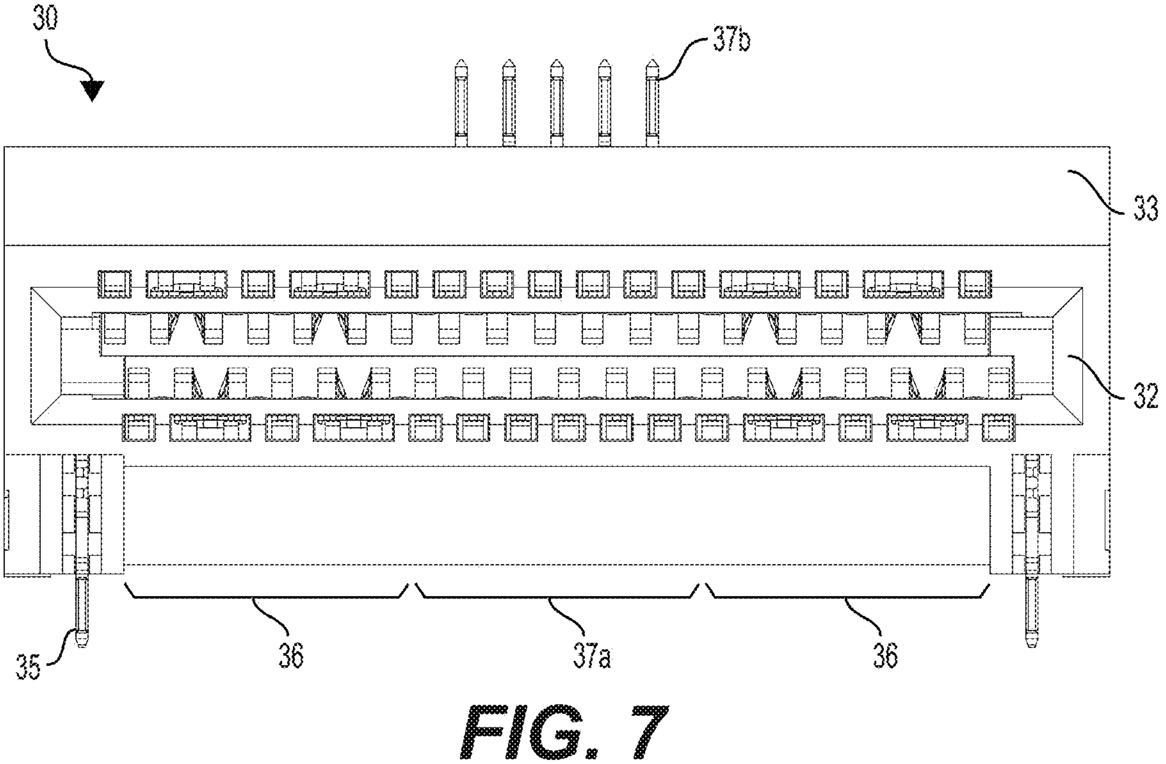
FIG. 7 is a front view of a connector body that can be used with the connector shown in FIGS. 4 and 5.
Figure 8:
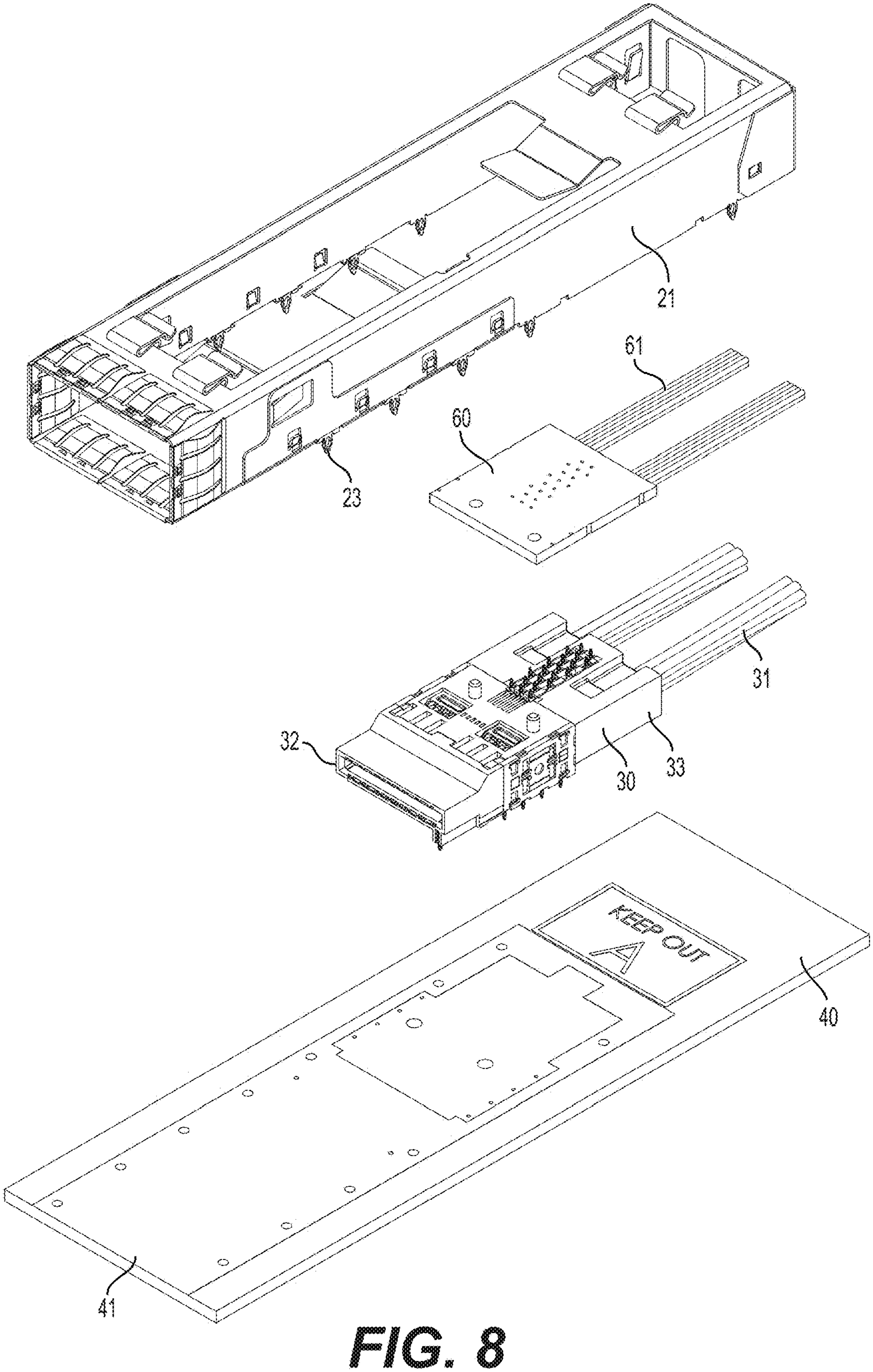
FIGS. 8 and 9 are front and rear exploded perspective views of the connector shown in FIGS. 4 and 5.
Figure 9:
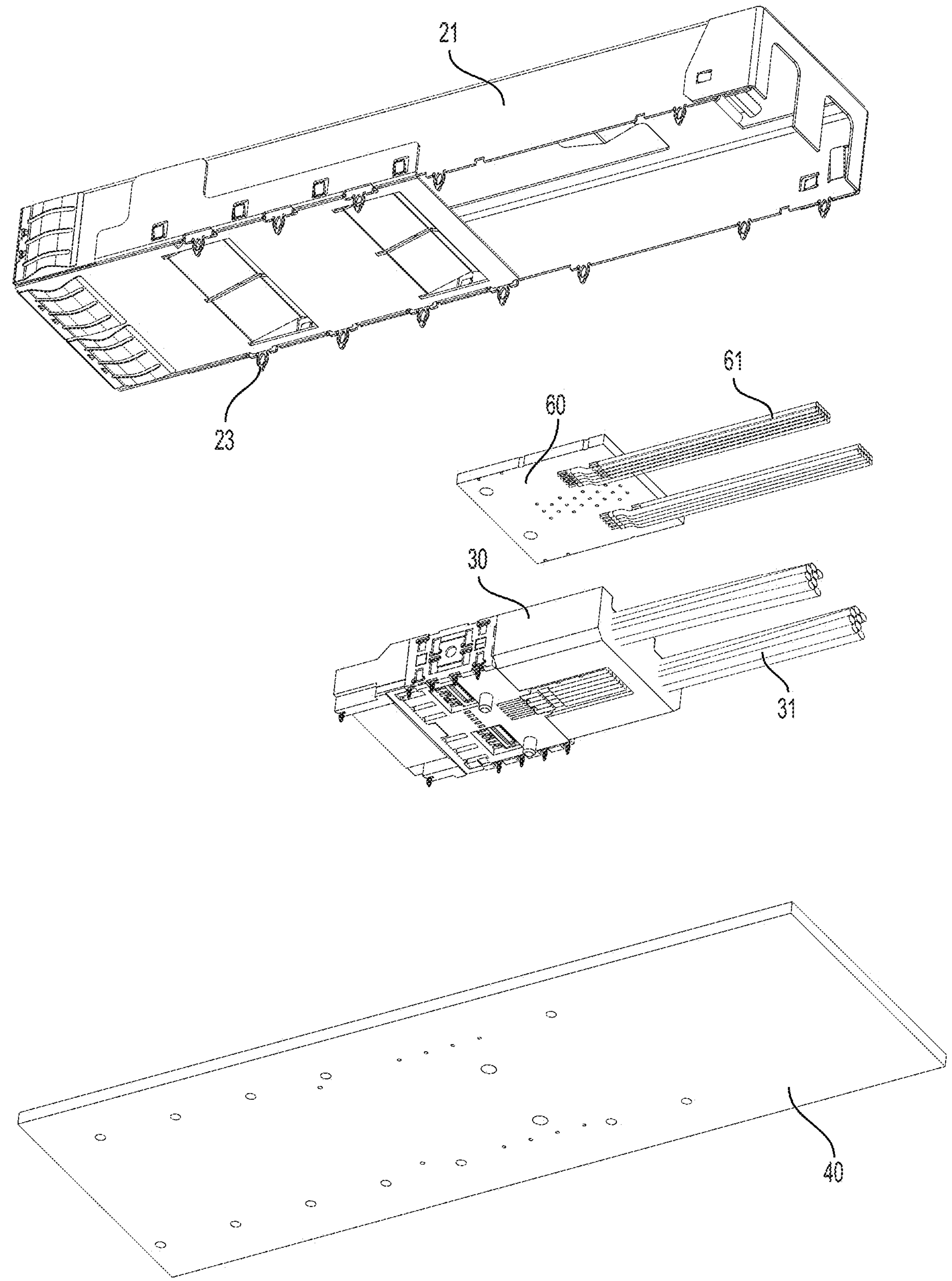

FIGS. 4 and 5 are front and rear perspective views of a connector 20 according to a first embodiment of the present invention. FIG. 6 is a cross-section view of the connector 20. FIG. 7 is a front view of the connector 20 shown in FIGS. 4 and 5. FIGS. 8 and 9 are front and rear exploded perspective views of the connector 20 shown in FIGS. 4 and 5.

Figure 18:
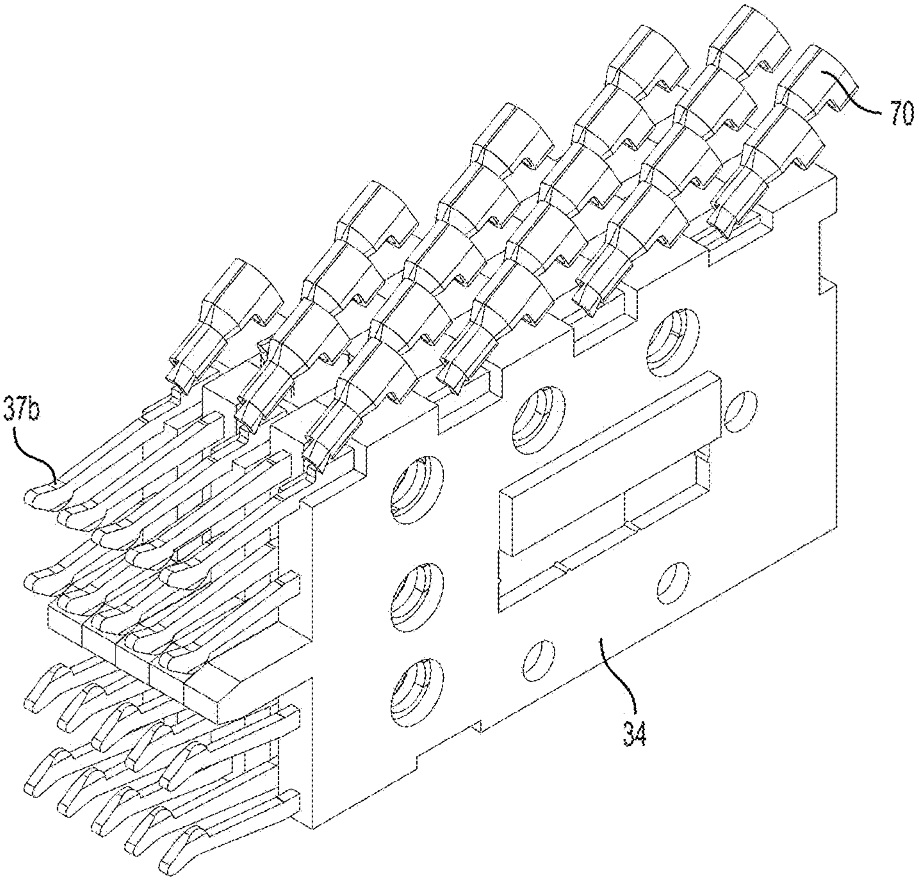
FIGS. 18 and 19 are views of a crimp connection to contacts.
Figure 19:
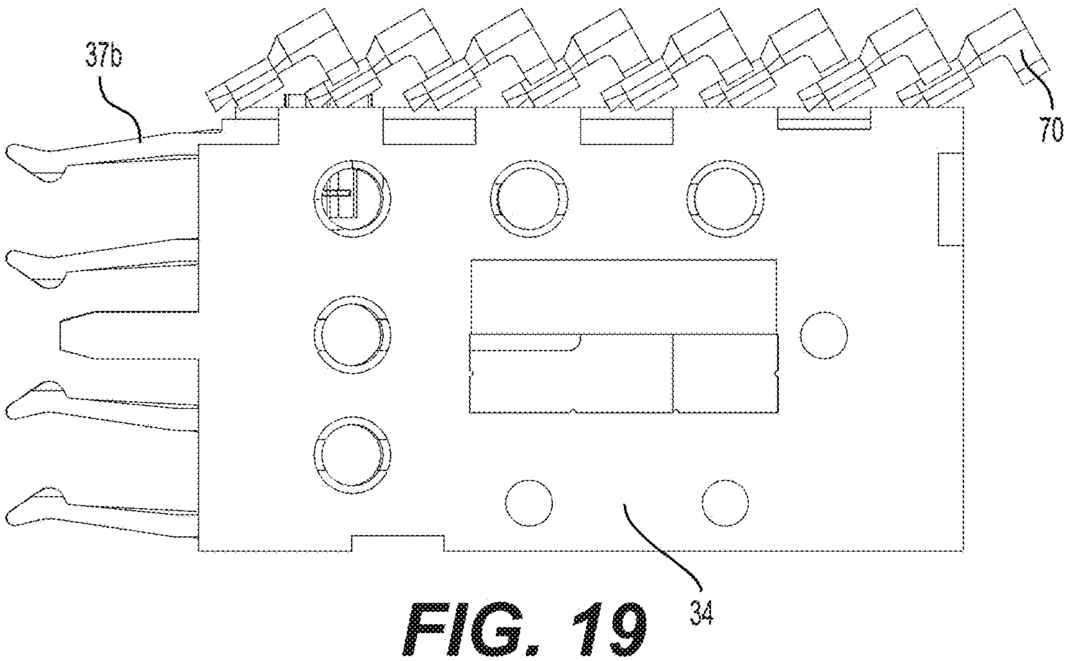

As shown in FIGS. 4-9, the connector 20 can include a connector body 30 with cables 31 extending from the connector body 30 and a control printed circuit board (PCB) 60 with PCB cables 61 extending from the control PCB 60. As shown in FIGS. 4 and 5, the PCB cables 61 can be attached to the bottom side, i.e., the side facing the connector body 30. The PCB cables 61 can be soldered to the control PCB 60 using, for example, laser, thermode, or hand solder. The PCB cables 61 can also be attached to the top side, i.e., the side opposite to the side facing of the connector body 30, if, for example, the crimps 70 shown in FIGS. 18 and 19 are used. All of the low-speed signals can be transmitted through the control PCB 60. It is also possible to transmit some low-speed signals through the control PCB 60 and some low-speed signals, e.g., ground and power, through the substrate 40. The connector 20, the connector body 30, or both can include electrically conductive, magnetic absorbing material, electrically non-conductive, magnetic absorbing material, or both.

Figure 10:
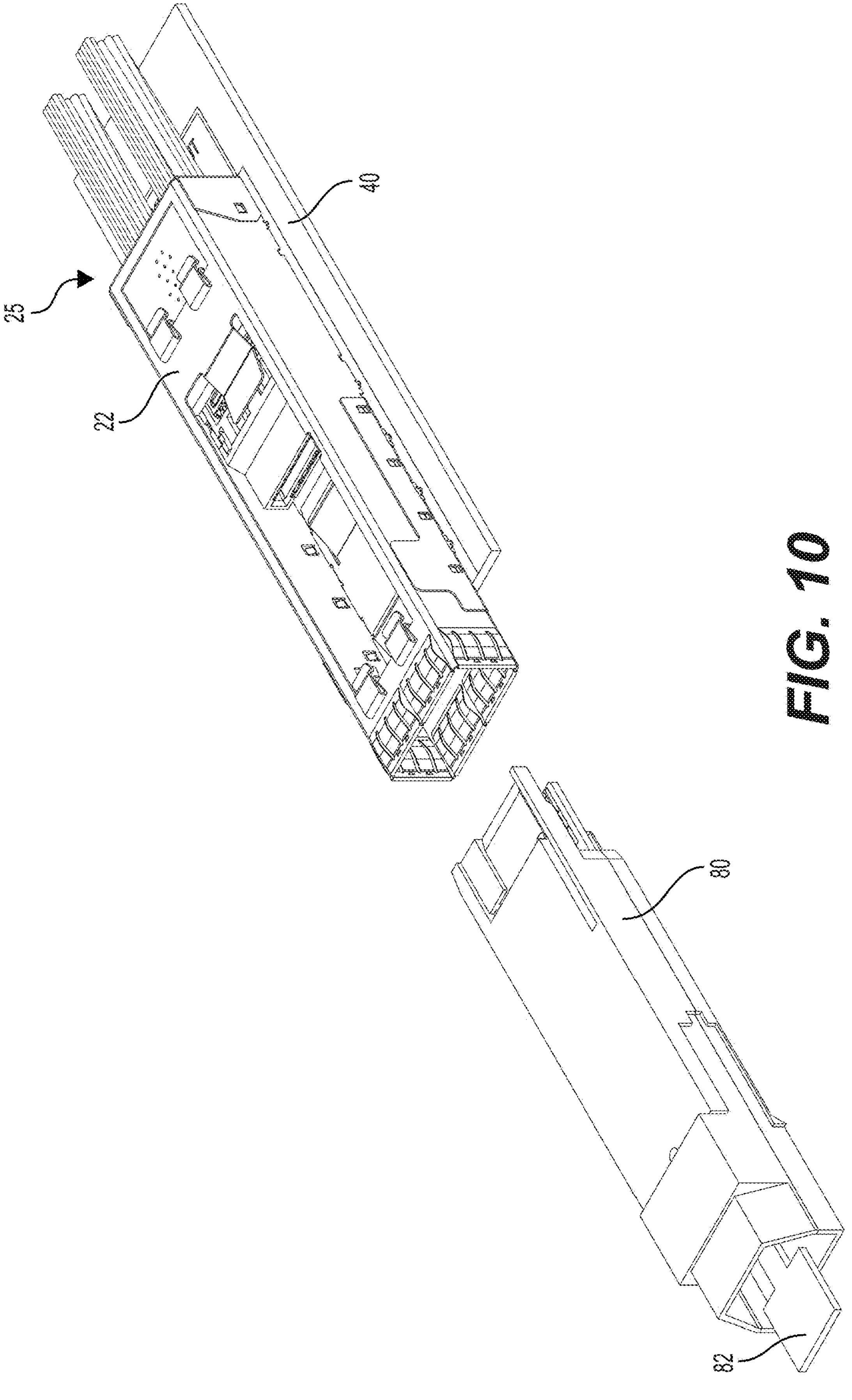
FIGS. 10 and 11 are top and bottom perspective views of the connector shown in FIGS. 4 and 5 arranged to mate with a male QSFP or similar connector.
Figure 11:
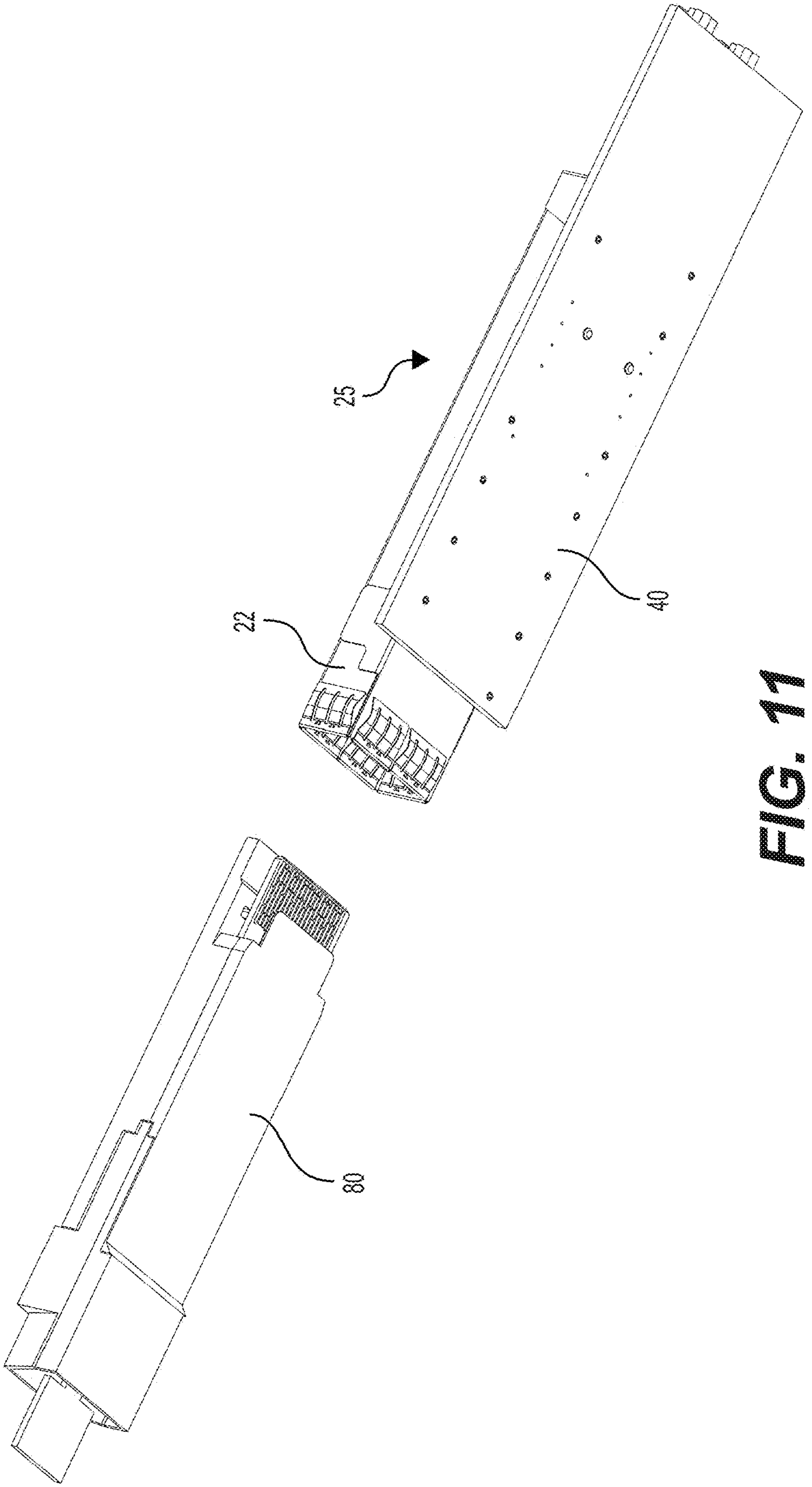

A cage 21 can surround the connector body 30 and the control PCB 60 and can receive a corresponding mating connector (not shown in FIGS. 4-9 but shown as mating connector in FIGS. 10 and 11). The cage 21 can include an open top, as shown, or be closed similar to the cage 21 shown in FIGS. 10 and 11. A heatsink (not shown) can be attached to the cage 21 such that the heatsink engages with the top of the mating connector through the opening. The control PCB 60 can be mounted to the connector body 30 that is mounted to a substrate 40. The substrate 40 can be a PCB, but other suitable substrates can also be used. The connector body 30 can include one or more alignment pins on the top connector body 30 to assist in aligning the control PCB 60 with the connector body 30. The control PCB 60 can include press-fit holes into which the press-fit tails of the contacts **37*b* of the second housing 33** can be inserted.

As shown in FIG. 7, the connector body 30 includes a first housing 32 and a second housing 33. The first housing 32 includes contacts 36 and **37*a*. The second housing 33 incudes contacts 37*b*. The contacts 36 can be high-frequency contacts that can be used to transmit high-speed signals, e.g., data signals, and the contacts 37*a* and 37*b* can be low-frequency contacts that can be used to transmit low-speed signals, e.g., control signals and power. The cables 31 and PCB cables 61 extend from the second housing 33. As shown in FIG. 6, the contacts 36 and 37*a* can be arranged in a double density arrangement. That is, the contacts 36 and 37*a* can be arranged on the top and bottom of the first housing 32 and arranged in two rows. Such an arrangement allows the contacts 36 and 37*a* to contact an edgecard inserted into the first housing 32** in two rows on both the top and bottom of the edgecard.

The first housing 32, the second housing 33, and the cage 21 can include edge pins 35 and cage pins 23 that mate with corresponding mounting holes in the substrate 40 to mechanically secure the connector 20 to the substrate 40. The edge pins 35 and the cage pins 23 can also provide a ground connection to a ground plane 41 or a ground trace in the substrate 40.

The second housing 33 can provide strain relief for the cables 31, and the cage 21 can provide a chassis ground connection for the connector 20 and can be in direct contact with the second housing 33 to help secure the connector 20 to the substrate 40. The cage pins 23 can engage with a ground plane 41 included in or on the substrate 40. The second housing 33 can include a grommet at an end of the second housing 33 that is opposite to the first housing 32. If included, the grommet can be an electromagnetic interference (EMI) grommet that is connected to the cage 21 and that can additionally be connected to the shields of the cables 31. The grommet can be molded to provide a secure, snap fit over the second housing 33 and/or to be inserted into the second housing 33.

The connector 20 can be a female connector. Although the connector 20 is shown as a receptacle connector configured to receive a mating card edge of a mating connector, such as a QSFP or QSFP+ or QSFP-DD connector, other connector/cable types may be used, including, for example, SAS/Mini SAS, HD Mini SAS, CX4, InfiniBand, SATA, SCSI, QSFP+, SFP+/SFP, HDMI Cable, USB Cable, Displayport Cable, CDFP, and other suitable connector/cable types. The first housing 32 can be configured so that it is compatible with male FSP or QSFP connectors.

The cables 31 are can be shielded electrical cables, for example, coaxial cables, twinaxial cables, triaxial cables, twisted pairs, flexible printed circuits, flat flexible circuits, etc. The cables can be arranged as differential-pair, twinaxial cables, for example. The cables 31 can connect to the substrate 40 at a distance of less than about 5 mm or about 10 mm from control circuitry, for example, so as to limit the length of the associated traces. Further, the length of the signal path through the cables 31 for high-speed signals can be longer than the length of the signal path though the substrate 40 to limit the distance through high-loss signal paths. The longer cables 31 allow for the high-speed signals to be transmitted over longer distances over the top of the substrate 40 than if the high-speed signals where transmitted through high-loss signal paths such as traces on or within the substrate, and the longer cables 31 allow for greater design freedom in locating any IC that receives or transmits the high-speed signals farther away from the connector 20.

The connector 20 can be configured similar to that of connector 25 so that a mating connector 80, as shown in FIGS. 10 and 11, is able to engage with the contacts of the first housing 32. As shown in FIGS. 10 and 11, the mating connector 80 can be attached to a mating cable (not shown in FIGS. 10 and 11) that can be used to connect an integrated PCB with other components that provide a complex electrical system, such as a computer, router, switching network, PCB control, or other suitable electrical systems. The mating cable can be, for example, a passive electrical cable, a shielded electrical cable, or an active optical cable. One example of a mating connector 80 including a pull-tab 82 is shown in FIGS. 10 and 11. As shown in FIGS. 10 and 11, the connector 25 can mate with, for example, a male QSFP connector, i.e., mating connector 80, with an attached mating cable. However, any similar connector may be used.

As shown in FIG. 7, the connector body 30 can include a total number and arrangement of contacts 36, 37*a*, 37*b*, for example, to be compatible with the QSFP-DD specification. However, other numbers and arrangements of contacts can be used. Further, FIG. 7 shows that the contacts 37*a* can be arranged in the center portion of the row of contacts between sets of the contacts 36 that are arranged at outside portions of the row of contacts. As shown in FIG. 7, the contacts 37*b* can be routed to extend upward at a right angle or substantially at a right angle within manufacturing tolerances to the contact row so that they can be terminated to the control PCB 60.

Figure 12:
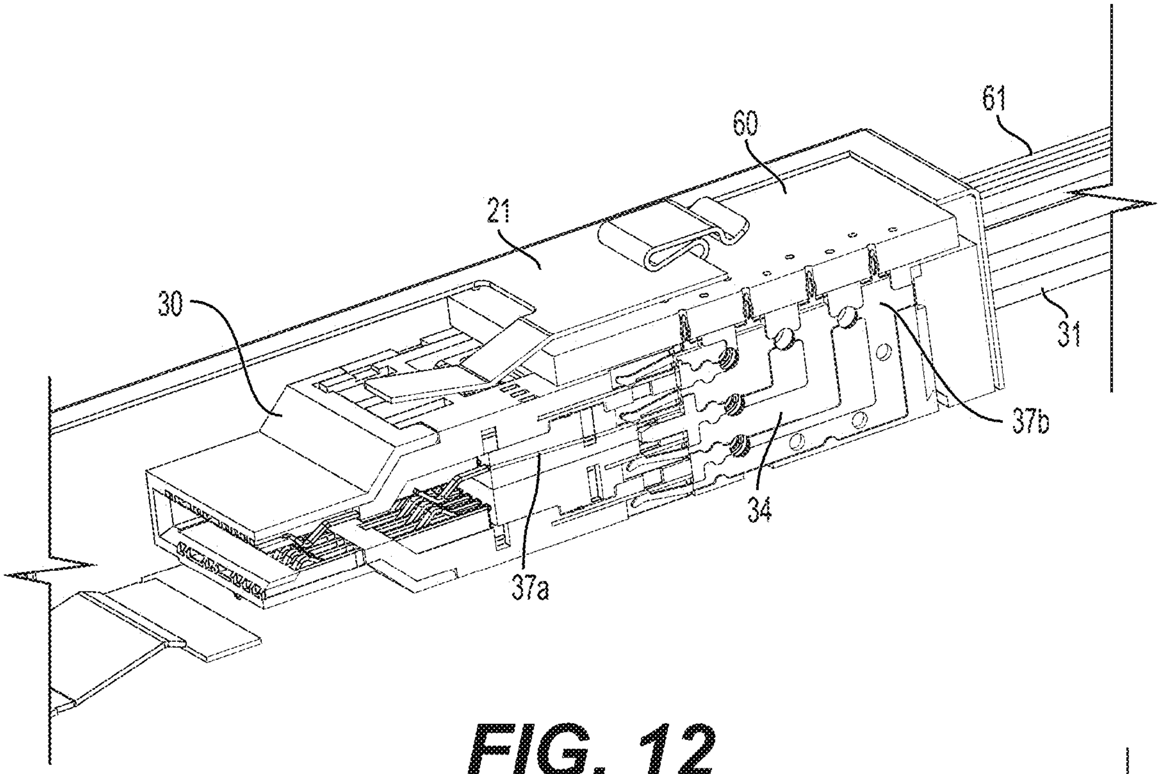
FIGS. 12 and 13 are cross-sectional views of the connector shown in FIGS. 4 and 5.
Figure 13:
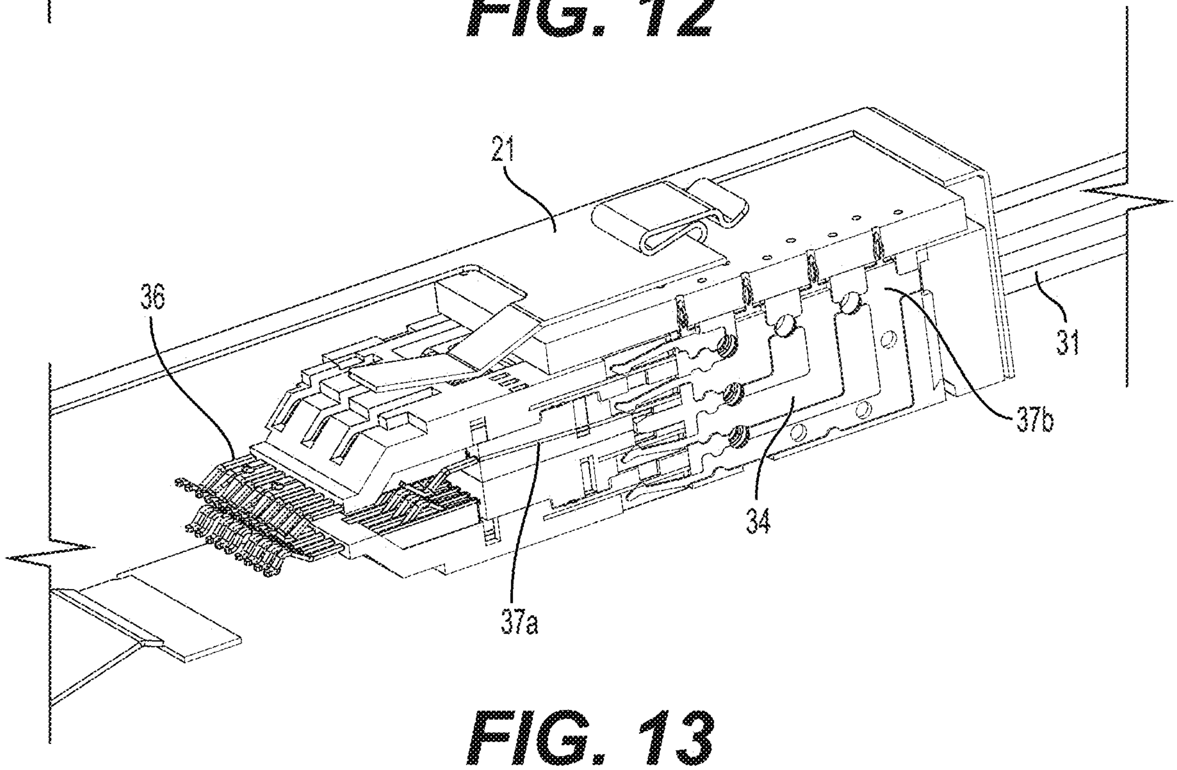
Figure 14:
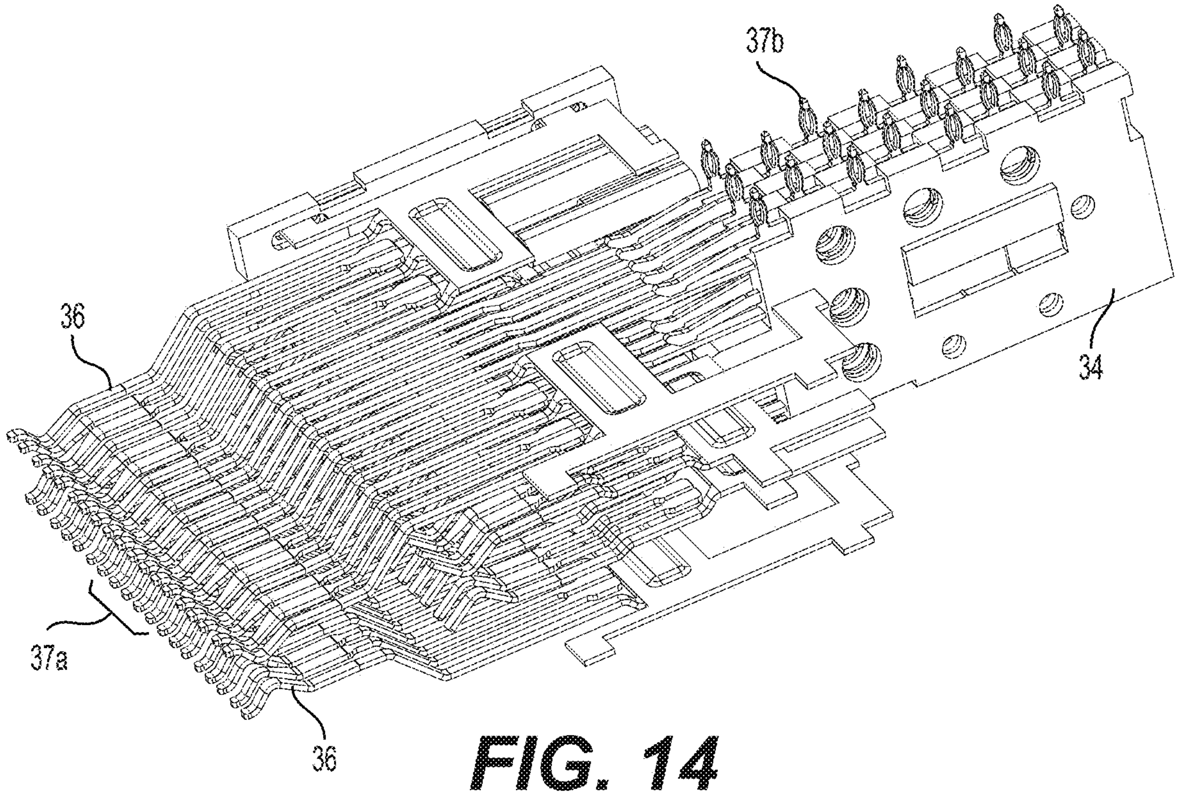
FIGS. 14 and 15 are close-up perspective views of contacts of the connector body shown in FIG. 7.
Figure 15:
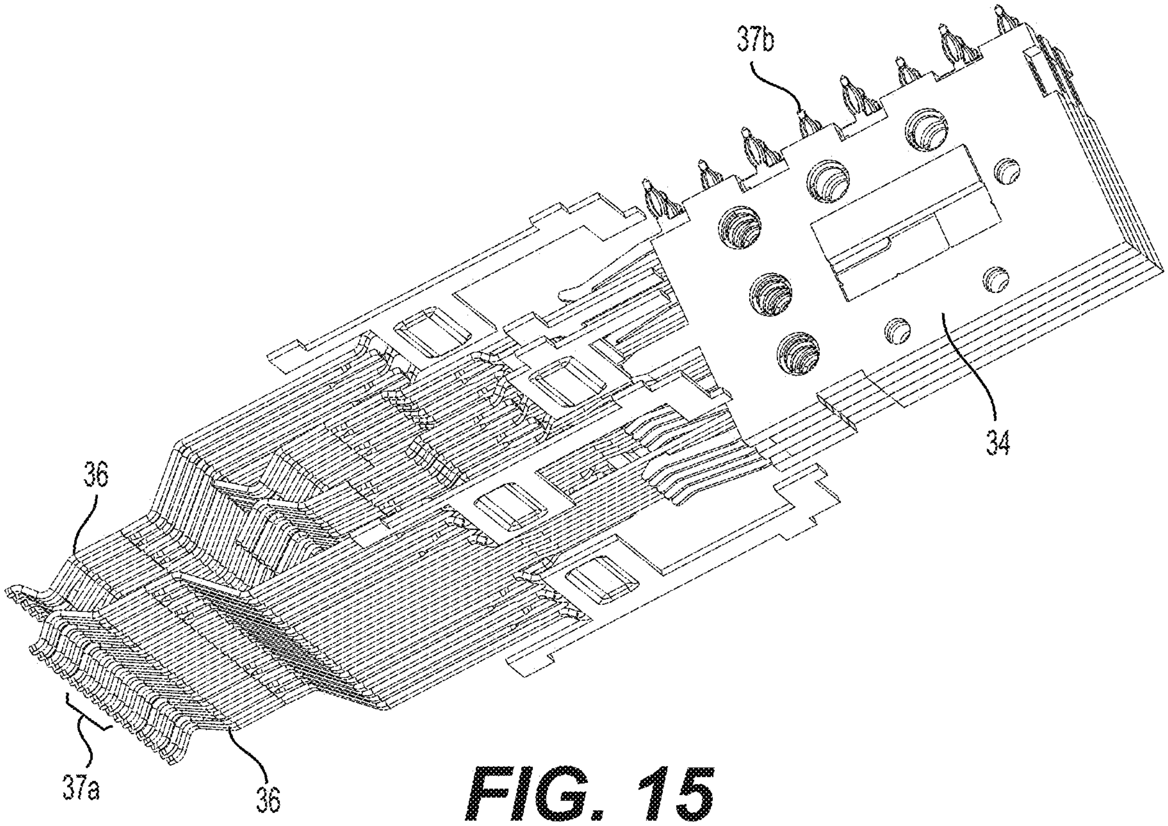
Figure 16:
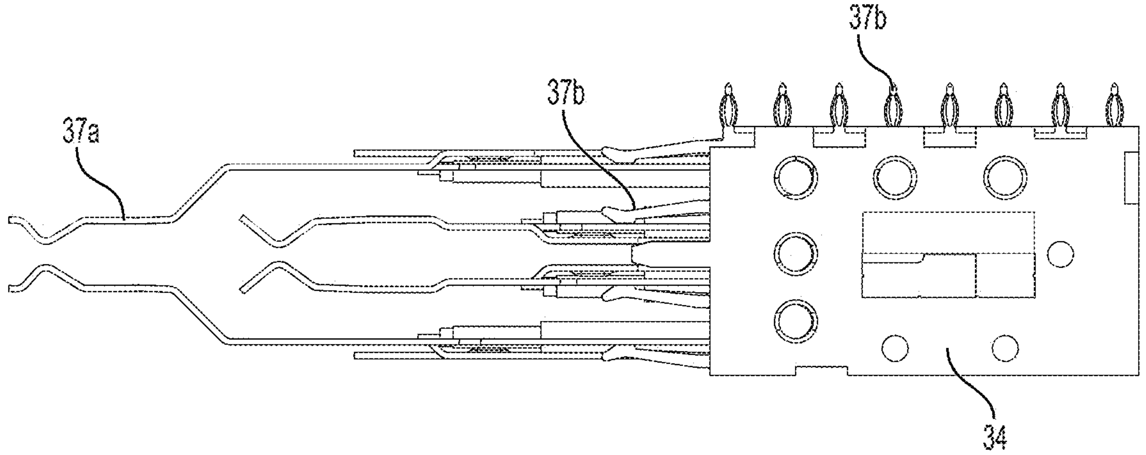
FIG. 16 is a side view of contacts of the connector body shown in FIG. 7.

FIGS. 12 and 13 are cross-sectional views of the connector 20 shown in FIGS. 4 and 5. For clarity, the substrate 40 is not shown in FIG. 12, and the first housing 32, the second housing 33, the cage 21, the substrate 40, and the control PCB 60 are not shown in FIG. 13. FIGS. 14 and 15 are close-up perspective views of contacts shown in FIGS. 12 and 13. FIG. 16 is a side view of the contacts shown in FIGS. 12-15.

Figure 17:
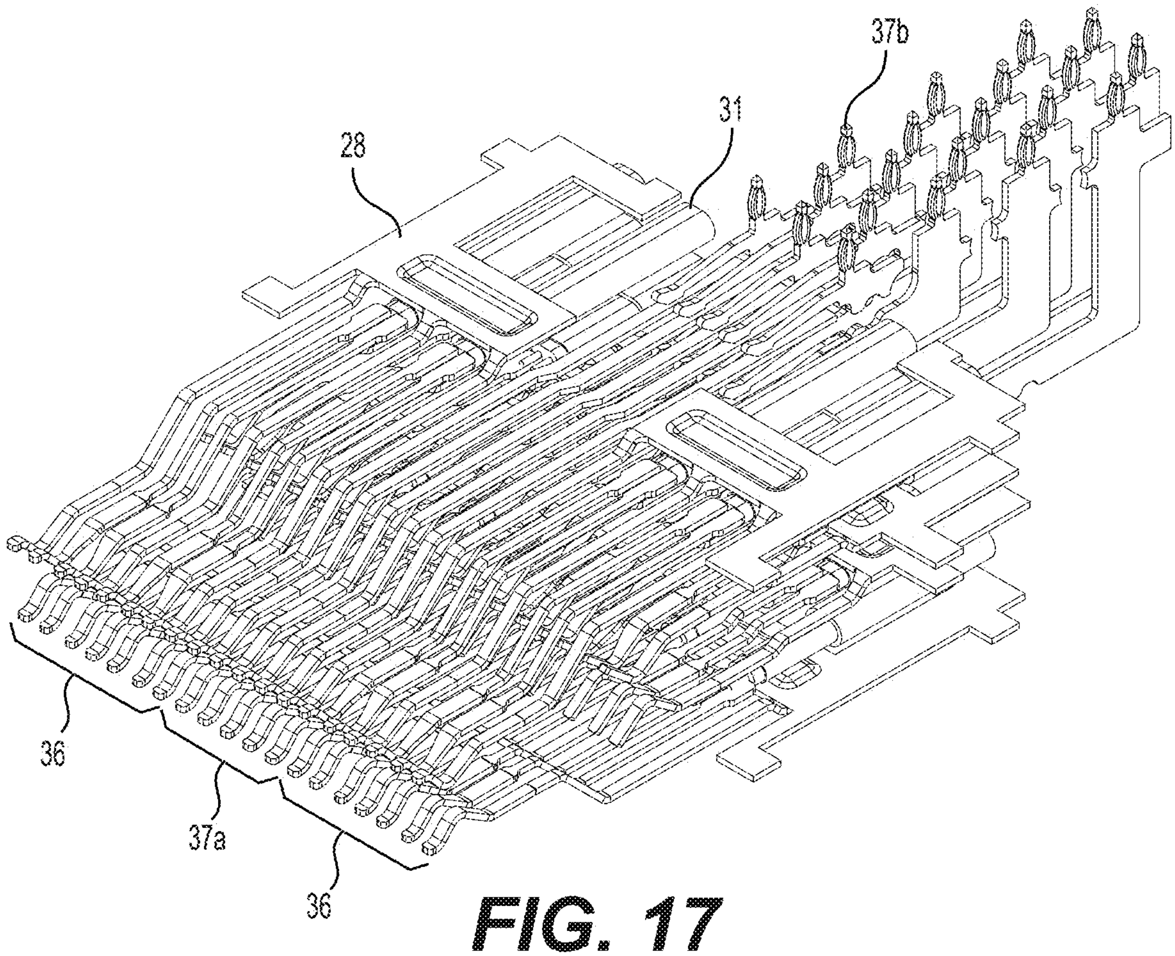
FIG. 17 is a perspective view of the connections between twinaxial cables and the contacts of the connector shown in FIGS. 4 and 5.

FIG. 17 shows the cable connection between some of the contacts 36 and the center conductor of a corresponding cable 31. For clarity, only a portion of the cables 31 is shown. These cable connections can be used to transmit high-frequency signals, but can also be used to transmit low-frequency signals, control signals, power, etc. The cables 31 can be twinaxial cables, which include two center conductors surrounded by a shield and an insulator disposed between the two center conductors and the shield. The cables 31 can be used with differential signaling to provide a high degree of signal integrity. The shield of the cables 31 is connected to the ground plane 28.

The connection between the contacts 36 and the cables 31 can be a fusible connection provided by lead-free solder, using a typical reflow soldering process. However, the contacts 36 and the cables 31 may also be connected by hand soldering, lead-based solders, crimping, ultrasonic welding, and other suitable connection structures.

As shown in FIG. 17, the contacts 36 can be configured so that the contacts that are connected to the center conductors of the cable 31 have an adjacent contact that is connected to ground. This allows the electrical paths through the connector 20 to be impedance-matched to the shielded electrical cable 31 and helps to minimize cross-talk between adjacent channels transmitted in adjacent electrical paths. Each high-frequency channel can include two shielded cables 31, one for transmitting and one for receiving. A ground connection can be included between the transmitting and receiving channels. Optionally, the contacts 36 can be initially connected by tie bars to provide a rigid structure that structurally supports the contacts 36 during manufacturing and assembling of the connector 20. The tie bars are then cut or stamped after the contacts 36 have been arranged in the first housing 32, and the first housing 32 can then be attached to the second housing 33.

FIG. 17 also shows contact connections between the contacts 37*a* and the contacts 37*b*. In the second housing 33, the contacts 37*b* are included in wafers 34. Each wafer 34 can include any number of contacts 37*b*, and any number of wafers 34 can be used. For example, FIG. 18 shows five wafers 34 with each wafer 34 including four contacts 37*b*. The wafers 34 can be made in any suitable manner, including being insert molded around the contacts 37*b*. The contacts 37*b* in the wafers 34 can include fingers that engage with corresponding contacts 37*a* in the first housing 32, when the second housing 33 is mated with the first housing 32. The contact connections can be used to transmit low-frequency signals, e.g., control signals, power, etc.

Further, the contacts 36, 37*a*, and 37*b* may be formed in various shapes. For example, the distance between the high-frequency contacts 36 used to transmit differential signals can be adjusted along the length of the contacts 36 to tune the impedance profile of the contacts 36. The contacts 37*b* in the second housing 33 include a right angle bend to route the low-speed signals toward the top of the connector body 30.

Instead of the cables 31 being directly attached to the connector 20 as discussed above, an interface can be added to the back of the connector 20 so that a cable 31 can be plugged into the interface.

Instead of using the control PCB 60, as shown in FIGS. 18 and 19, a crimp 70 can be used at the end of each of the contacts 37 in the wafers 34 to attach the cables (not shown in FIGS. 18 and 19) to the contacts 37*b* in the wafers 34. The crimps 70 can be angled at any suitable angle. Angling the crimps 70 at 30° or about 30° within manufacturing tolerances allows for the connector to have the lowest profile. Optionally, any other suitable interface can be used.

Figure 20:
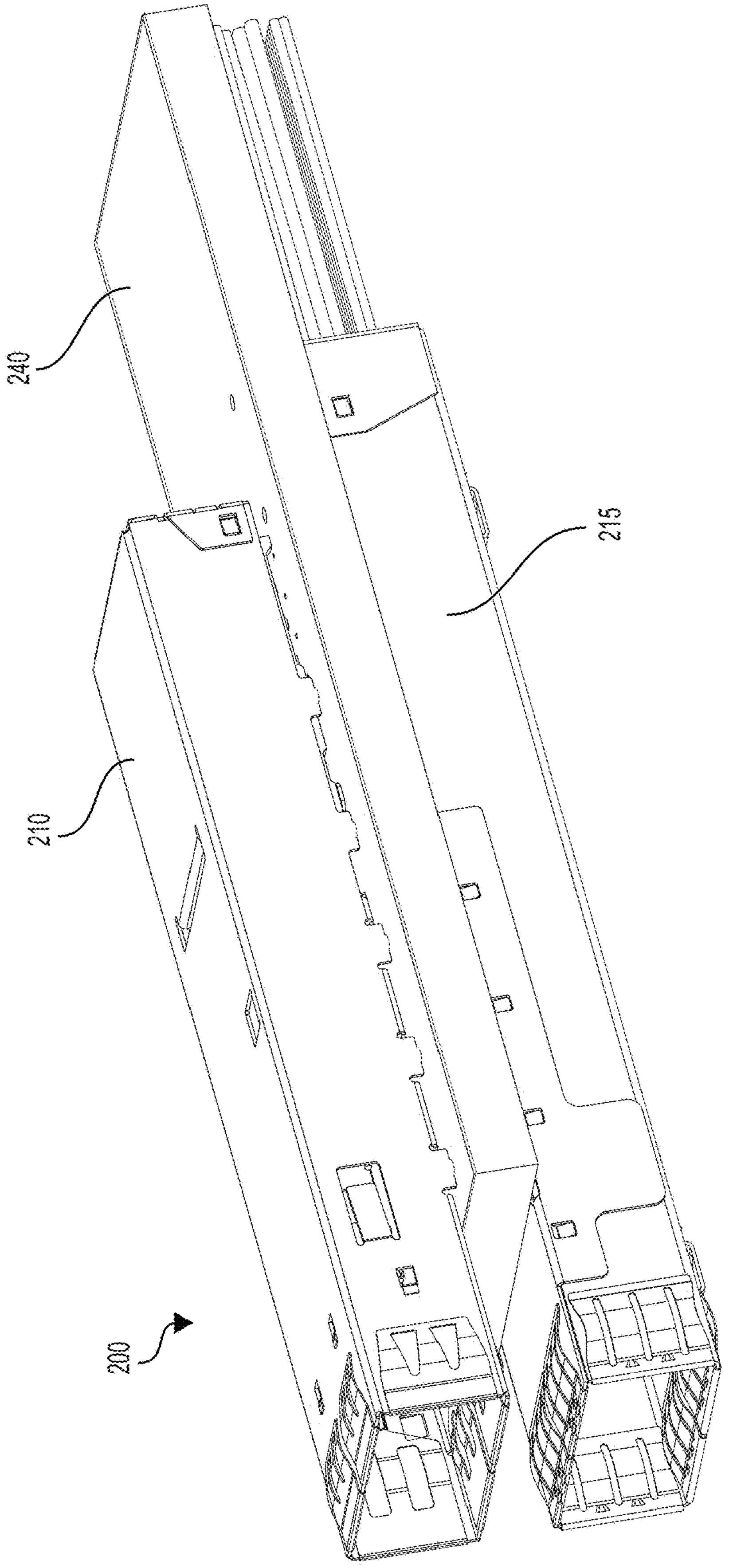
FIGS. 20-24 are views of a connector according to a second embodiment of the present invention.
Figure 21:
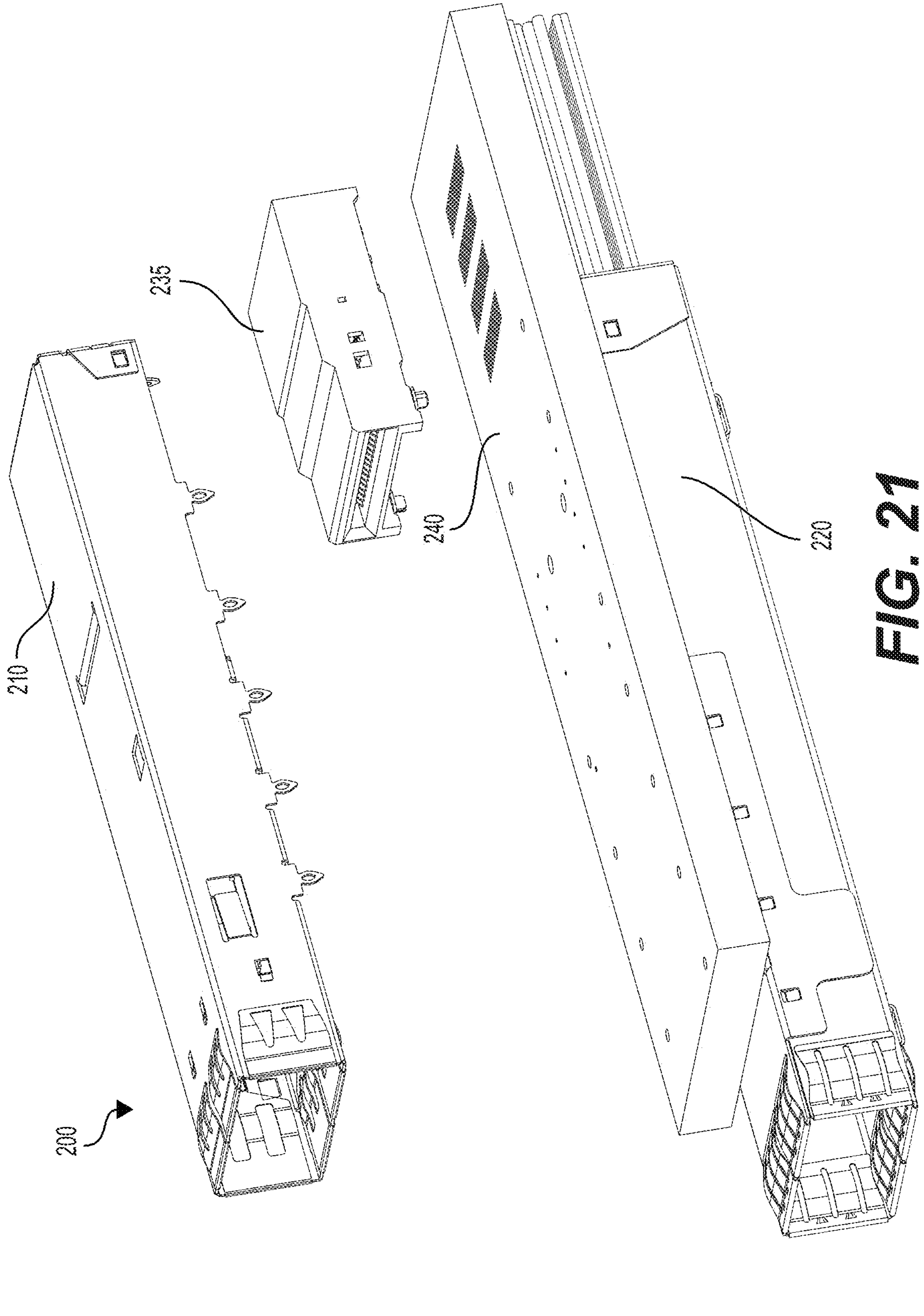
Figure 22:
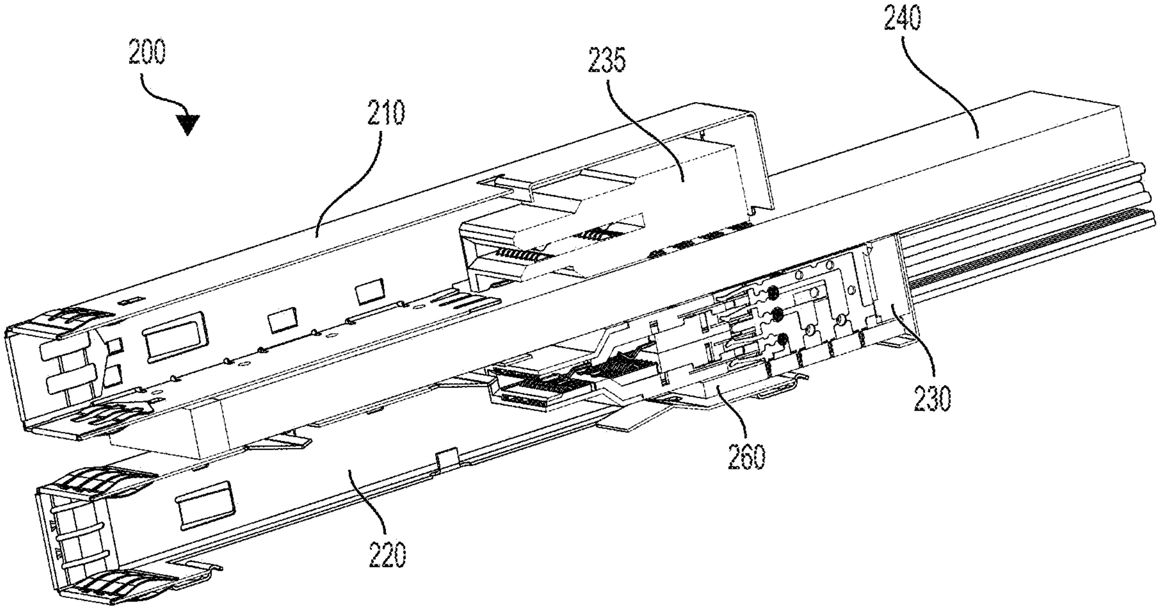
Figure 23:
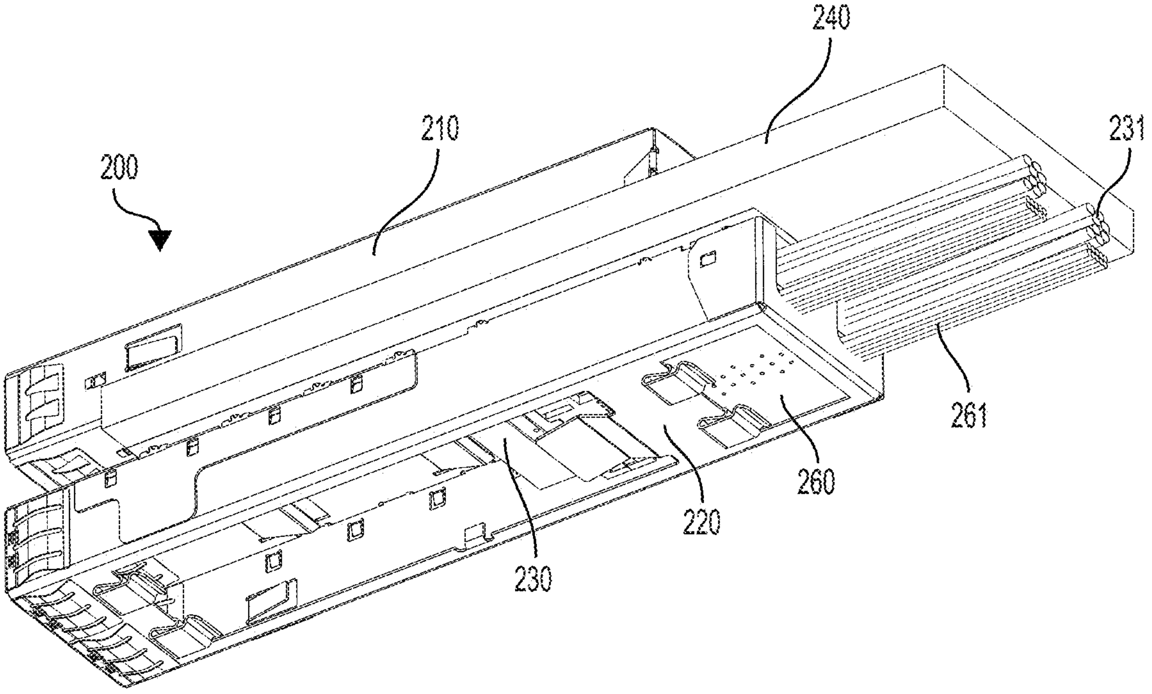
Figure 24:
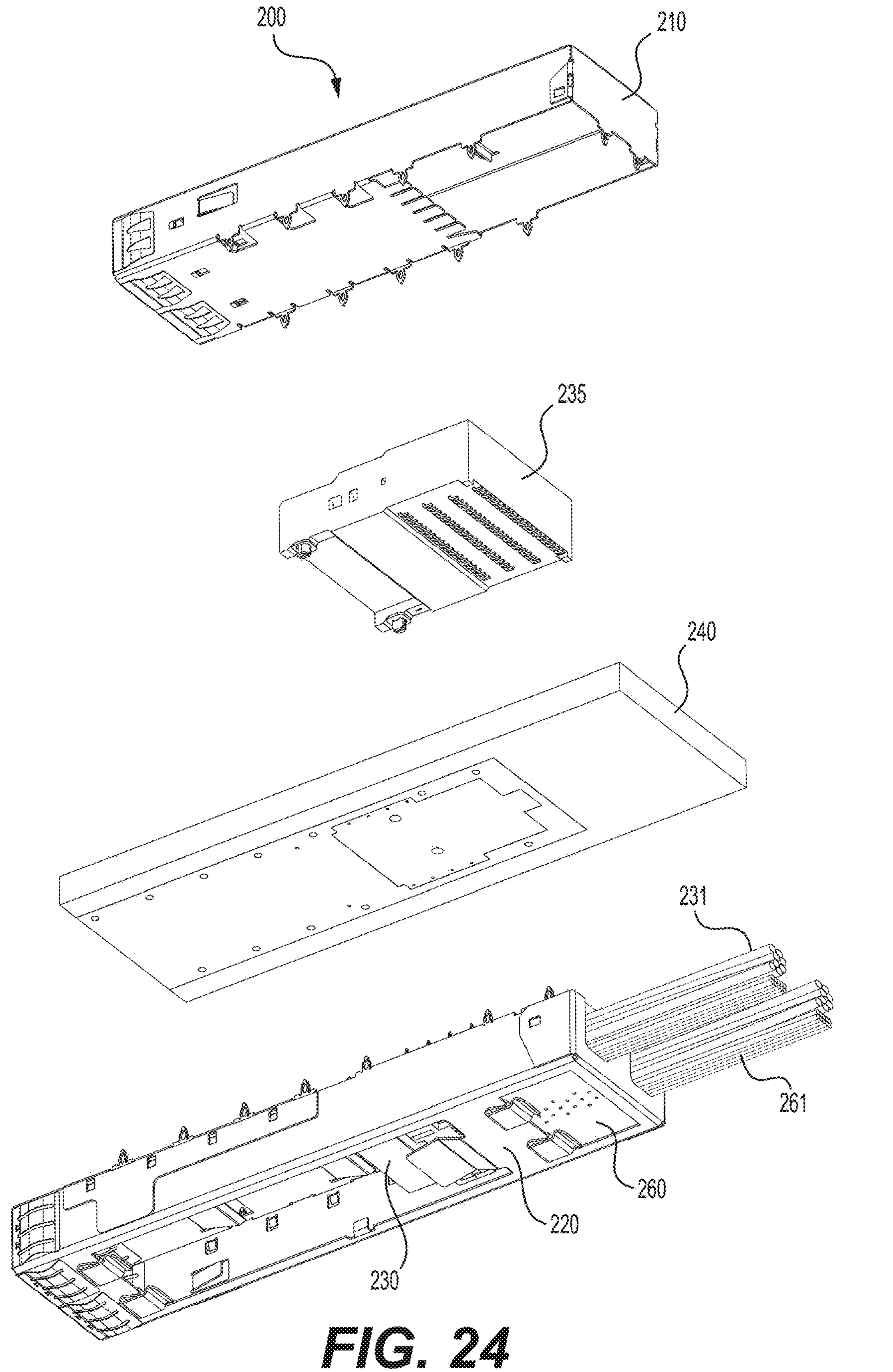

FIGS. 20-24 are perspective views of a connector 200 according to a second embodiment of the present invention. FIG. 20 is a top perspective view of the connector 200. FIG. 21 is partially exploded view of the connector 200. FIG. 22 is a sectional view of the connector 200. FIG. 23 is a bottom perspective view of the connector 200. FIG. 24 is an exploded view of the connector 200. As shown in FIGS. 20-24, the connector 200 is a belly-to-belly configuration that can include two cages 210 and 215 with respective connector bodies mounted on one substrate 240. The bottom cage 215 can include a connector body 230, a control PCB 260, and a substrate 240 are similar to the configuration described above. The top cage 210 can include a connector body 235, as shown in FIGS. 21, 22, and 24. The addition of a second cage and connector system increases the available contacts for connection and routing of signals (i.e. high frequency, low frequency, control signal, power, ground, etc.). The connector body 235 is similar to that described above, but may not include a control PCB with cables. The connector body 235 can be surface mounted to the substrate 240. The array contacts of the connector body 235 can be physically and electrically connected to a corresponding array of surface mount pads located on the substrate 240. Alignment pins on the connector body 230 can be arranged not to interfere with the footprint of the upper cage 210 and connector body 235.

The bottom perspective view in FIG. 23 and the exploded view of FIG. 24 show that the bottom connector 220 includes a cage 220, a connector body 230 with cables 231, and a control PCB 260 with PCB cables 261.

The top connector 210 and the bottom connector 220 can be mounted in a belly-to-belly configuration because the top connector 210 mating interface footprint does not interfere with the bottom connector 220 mating interface footprint. There is no interference because the low-speed signals of the bottom connector 220 are routed through cables instead of the substrate 240, which eliminates the need to have an array of press-fit holes in the substrate 240 to route the low-speed signals. In addition, weld tabs and/or alignment pins of the bottom connector 220 can be arranged so as not to interfere with the mating interface footprint of the top connector 210.

Figure 25:
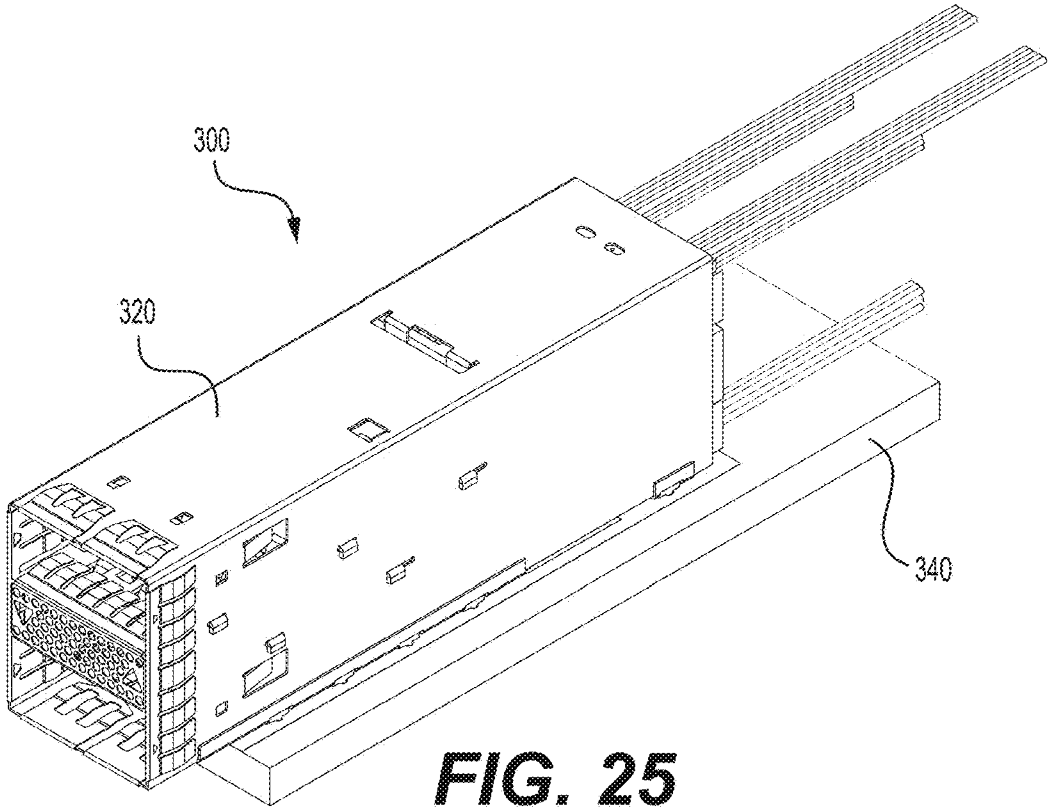
FIGS. 25-27 are perspective views of a connector according to a third embodiment of the present invention.
Figure 26:
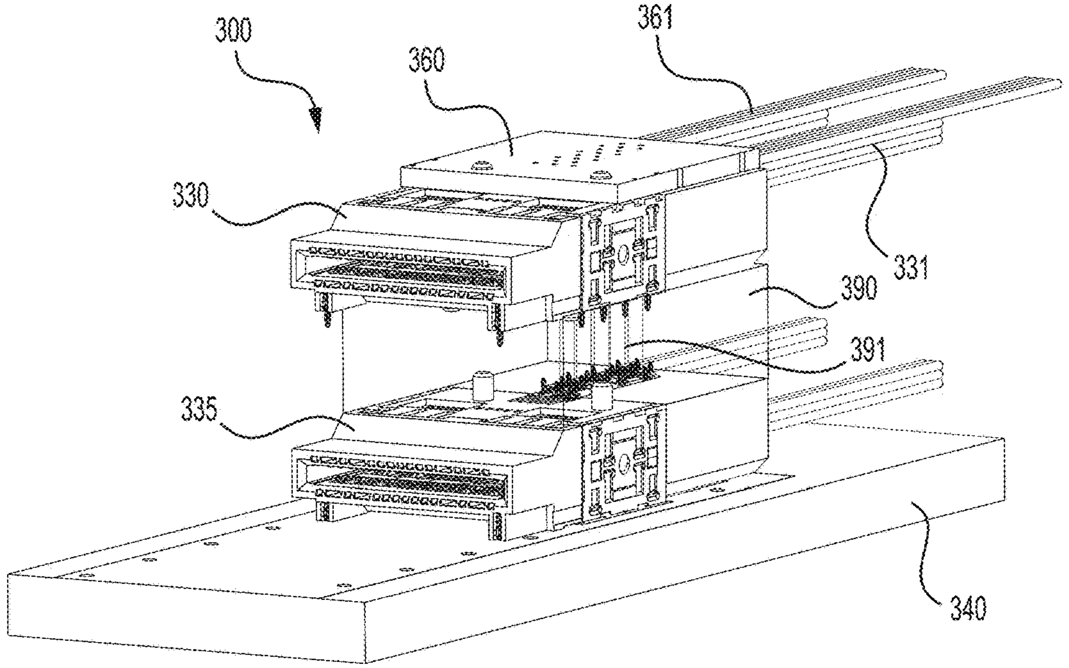
Figure 27:
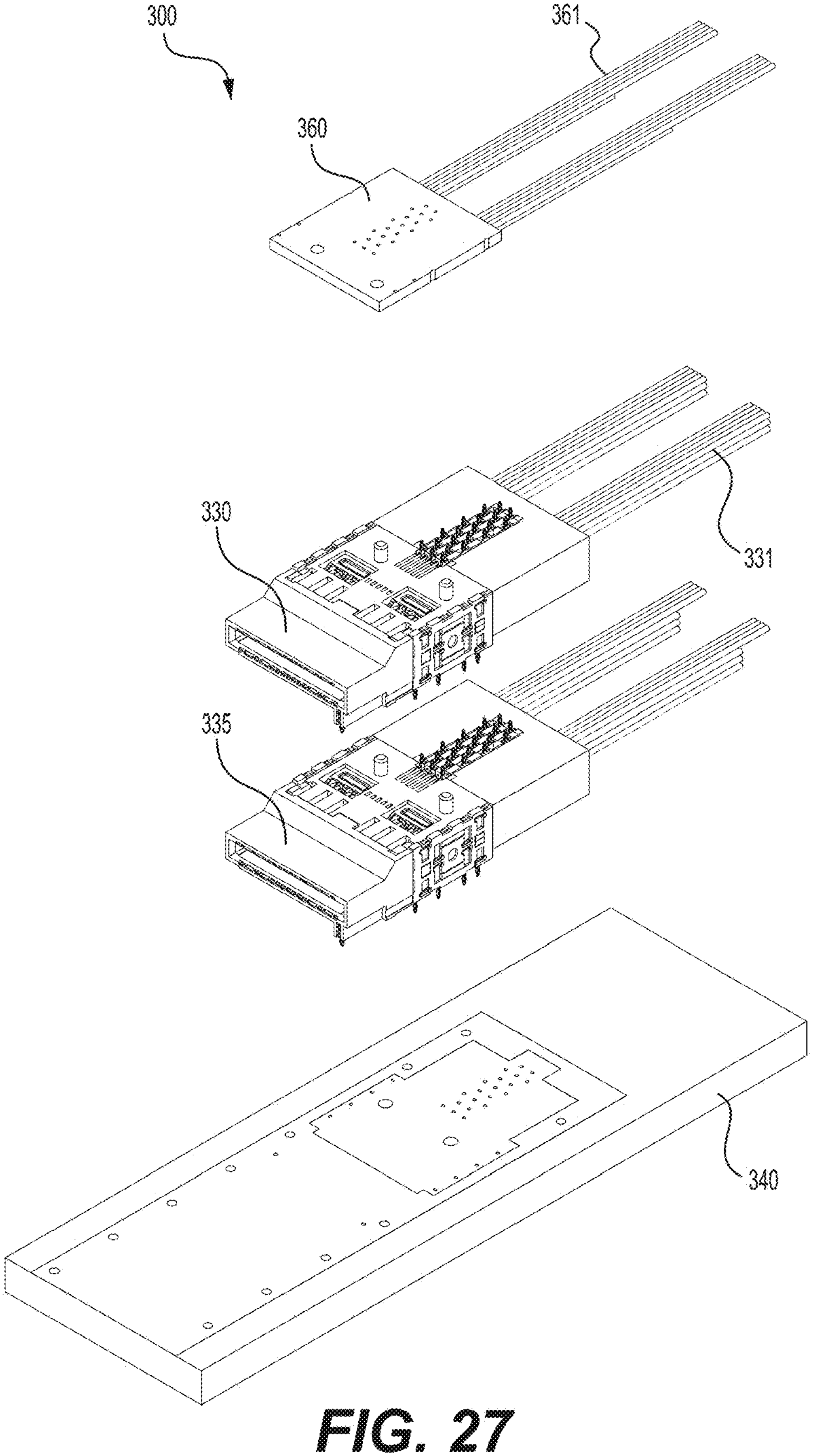

FIGS. 25-27 are perspective views of a connector 300 according to a third embodiment of the present invention. As shown in FIGS. 25-27, connector 300 is a double stack configuration including one cage 320 with two connector bodies 330 and 335 mounted on one substrate 340. The addition of a second connector system increases the available contacts for connection and routing of signals (i.e. high frequency, low frequency, control signal, power, ground, etc.).

The bottom connector body 335 can be similar to connector bodies described above, but without the control PCB. The bottom connector body 335 can route high-speed signals through cables and can route some or all of the low-speed signals through the spacer 390 to the control PCB 360 and the PCB cable 361 on top of the top connector body 330. Any low-speed signals that are not routed to the control PCB 360 can be routed to the substrate 340. The bottom connector body 335 can include contacts with press-fit tails that can be mated with the vias in the spacer 390. The top connector body 330 can also be similar to those described above, and can include a control PCB 360 with PCB cables 361. It is also possible to use crimps instead of a control PCB 360 so that the PCB cables 361 are crimped to the contacts, as shown in FIGS. 18 and 19. The top connector body 330 can include contacts with press-fit tails that also can be mated with the vias in the spacer 390. The top connector body 330 can also have contacts without press-fit tails that provide an electrical path between the top connector body 330 and the control PCB 360, without going through the spacer 390.

The top perspective view of FIG. 26 and the exploded view of FIG. 27 show the connector 300 without the cage 320. The top connector body 330 includes cables 331 and the control PCB 360 with PCB cables 361. The bottom connector body 335 can be attached directly to the substrate 340. FIG. 26 shows a spacer 390 as a mounting structure between the top connector body 330 and the bottom connector body 335. For clarity, the spacer 390 is shown as transparent so that the vias 391 between the top connector body 330 and the bottom connector body 335 can be seen. The spacer 390 can commonly connect some low-speed signals together, and the spacer can commonly connect ground and/or power from both the top connector body 330 and the bottom connector body 335. For example, ground contacts of the top connector body 330 and the bottom connector body 335 can be commonly connected together by being connected to the same via in the spacer 390.

Routing some or all of the low-speed signals of the top connector body 330 and the bottom connector body 335 through the spacer 390 allows for a belly-to-belly configuration, in which another connector can be connected on a surface opposite to the surface of the substrate 340 on which the connector 300 is mounted, similar to the configuration shown, for example, in FIGS. 20-24.

Figure 28:
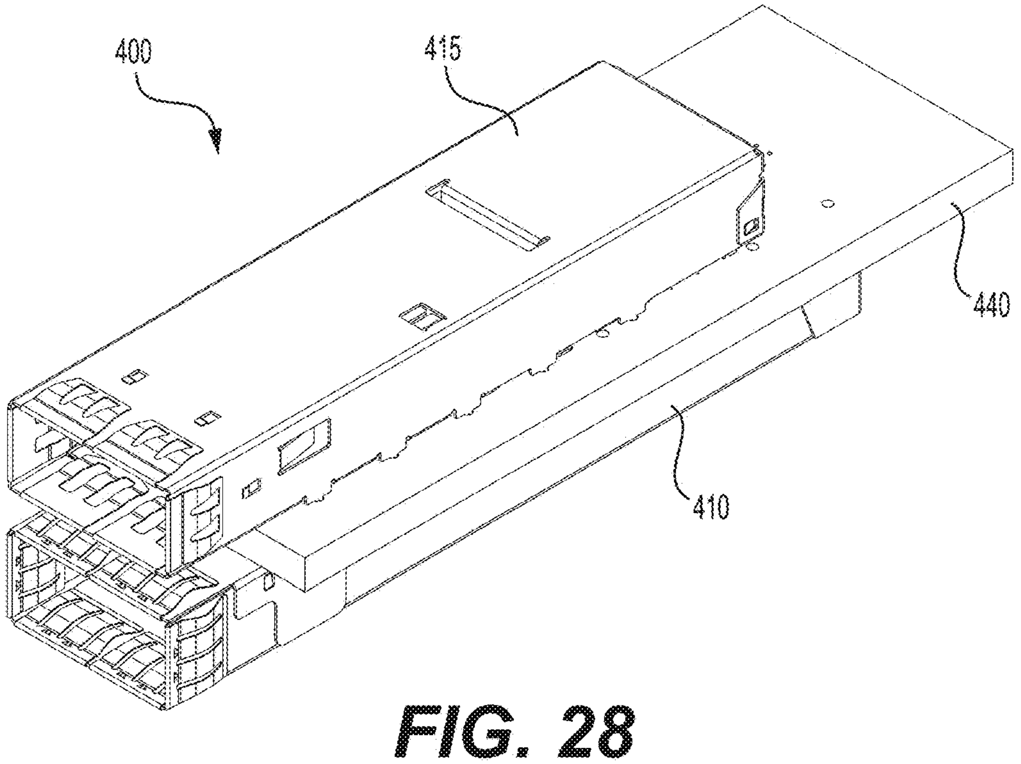
FIGS. 28-30 are perspective views of a connector according to a fourth embodiment of the present invention.
Figure 29:
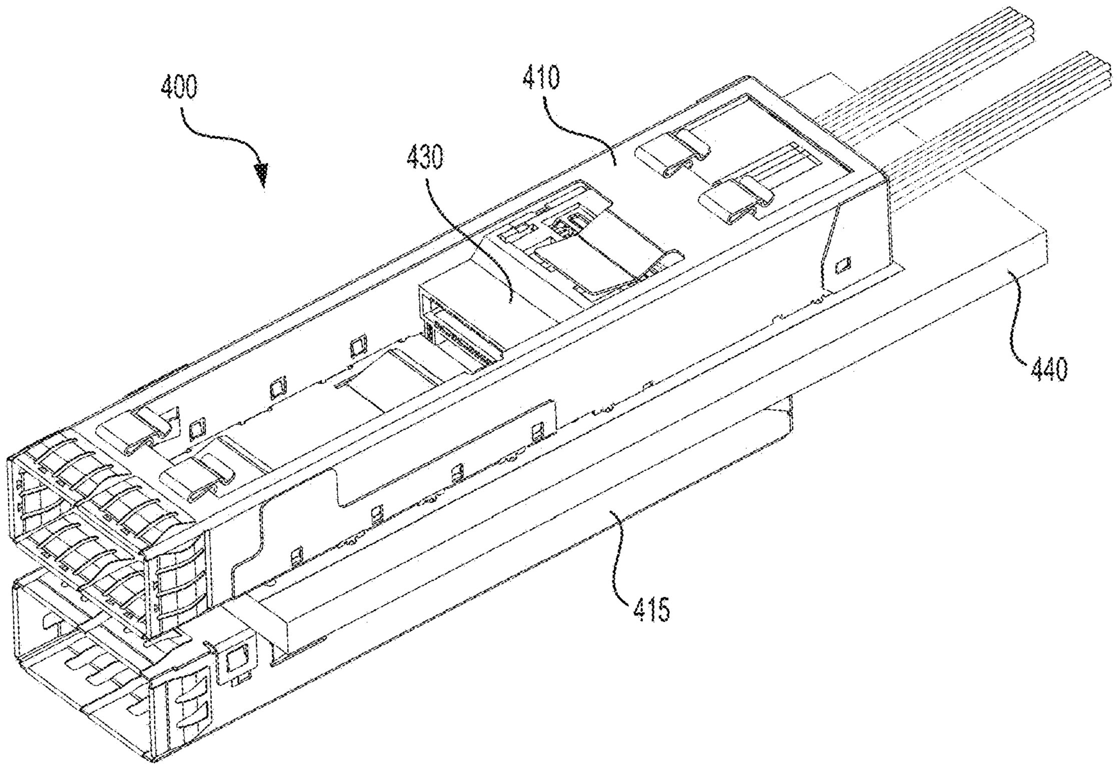
Figure 30:
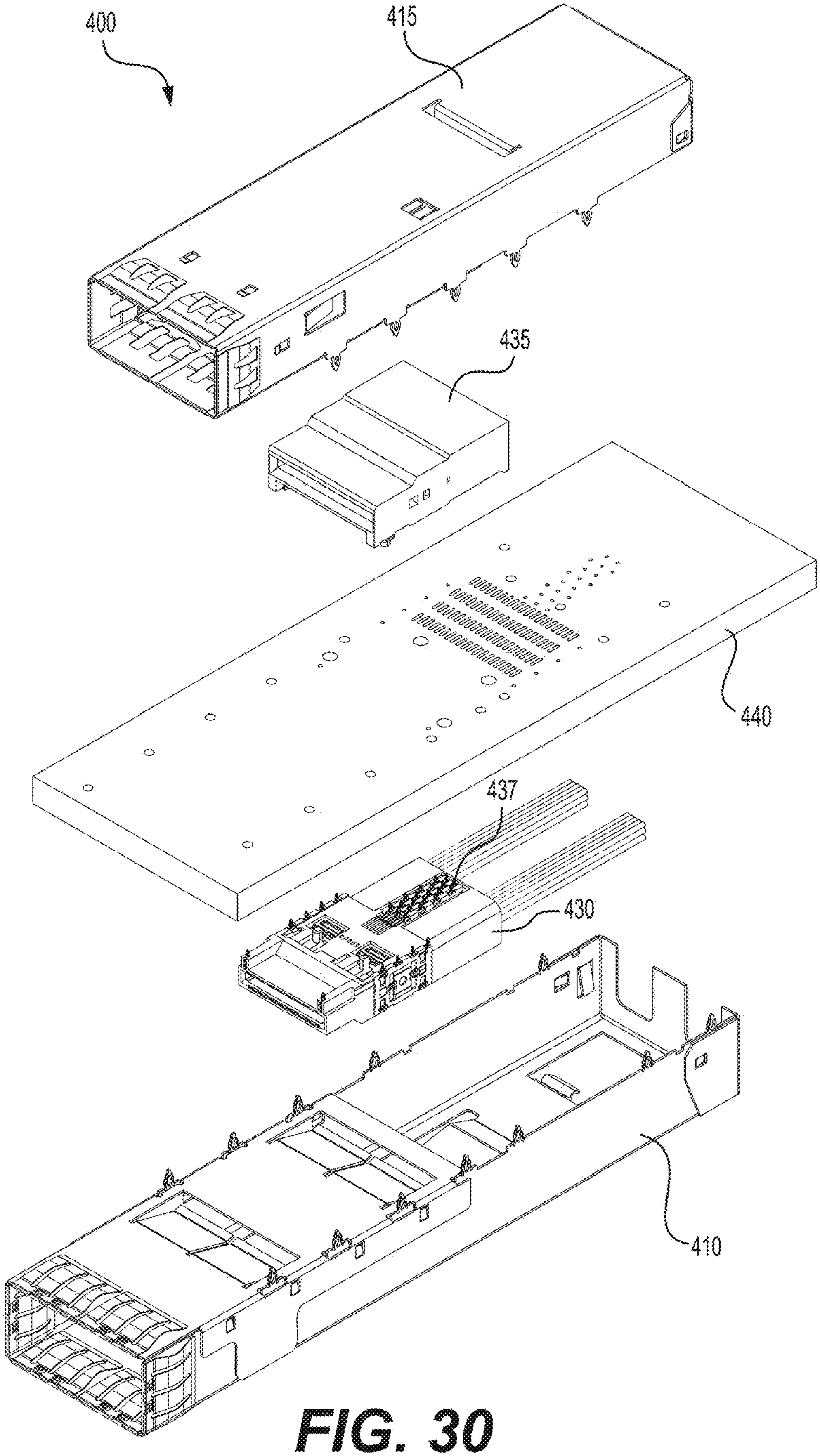

FIGS. 28-32 are perspective views of a connector 400 according to a fourth embodiment of the present invention. As shown in FIGS. 28-30, connector 400 has a belly-to-belly configuration including two cages 410 and 415 with the bottoms of respective connector bodies 430 and 435 mounted on one substrate 440. The addition of a second cage and connector system increases the available contacts for connection and routing of signals (i.e. high frequency, low frequency, control signal, power, ground, etc.).

Figure 31:
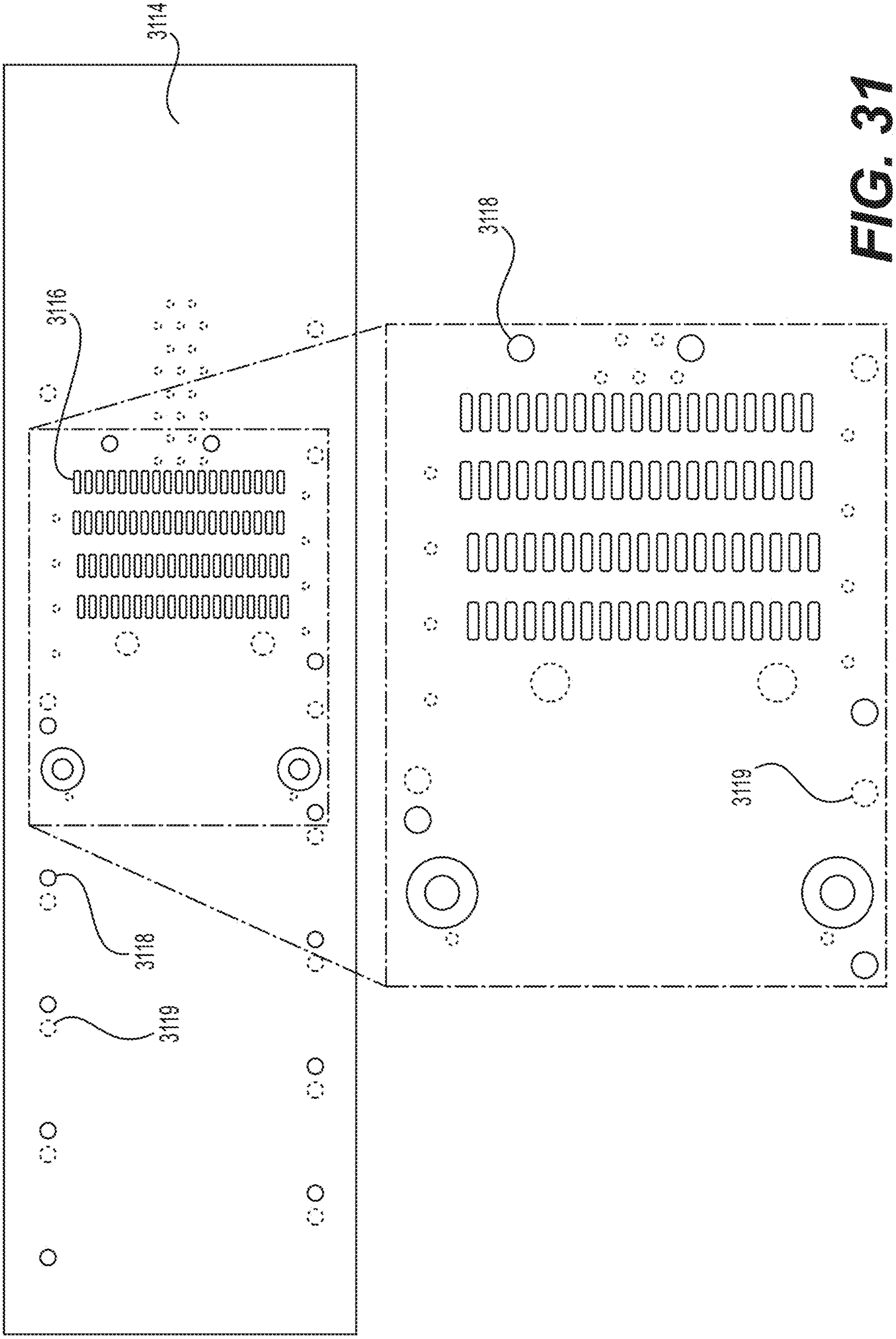
FIG. 31 shows a plan view of a footprint of the connector according to the fourth embodiment of the present invention.
Figure 32:
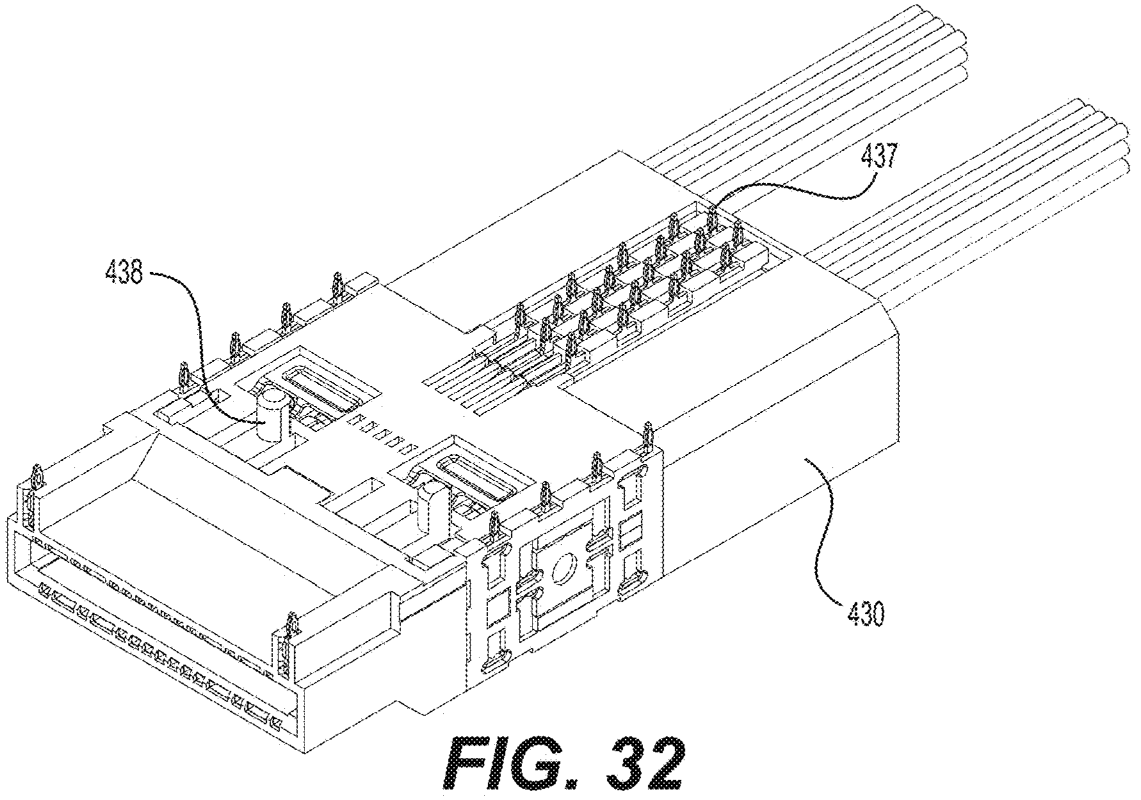
FIG. 32 is a perspective view of a connector body according to the fourth embodiment of the present invention.

The connector bodies 430 and 435 can be similar to those described above, but may not include a control PCB with cables. However, as shown in FIGS. 30 and 32, the contacts 437 of the connector body 430 can be oriented to be mounted to the substrate 440 rather than to a control PCB. As shown in the footprint of FIG. 31, the contacts 437 and the alignment pins 438 can be arranged such that the array of holes required by the press-fit tails of the contacts 437 and by the alignment pins 438 do not interfere with the footprint of the top connector 435 when the contacts 437 are mounted to the substrate 440. In FIG. 31, the footprint of the top connector body 435 on the substrate 3114 is shown in dashed lines and includes lands 3116. Holes 3118 for mounting the top connector body 435 and the cage 415 are shown in solid lines, and the holes 3119 for mounting the bottom connector body 430 and cage 410 is shown in broken lines.

Figure 33:
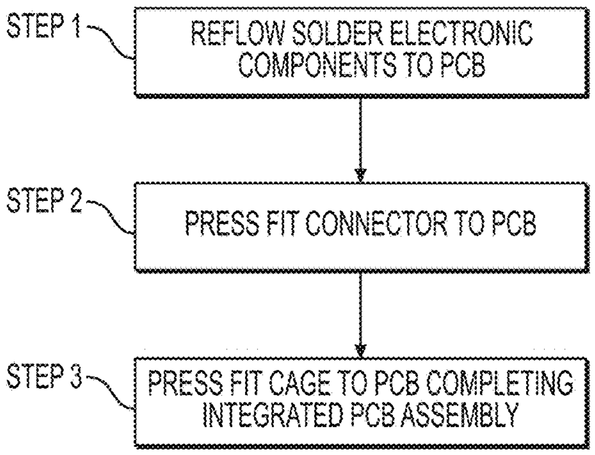
FIG. 33 is a diagram showing a method of assembly for an integrated PCB assembly.

FIG. 33 is a diagram showing a method of assembly for an integrated substrate or PCB. The method shown in FIG. 33 can be used, for example, to assemble a PCB that includes the connector shown in FIGS. 4 and 5 attached to a PCB.

As shown in step 1, electrical components (for example, ICs, capacitors, and the like) may be attached to the PCB using a standard reflow solder process before the connector is attached. That is, the electrical components may be surface-mount components. However, the electrical components may alternatively be attached to the PCB by press-fit connections. As shown in step 2, the connector is then press-fit to the PCB. The IC connector may also be press-fit to the PCB in step 2. Press-fitting the connector(s) to the PCB provides sufficient electrical and mechanical connections between the connector(s) and the PCB to ensure that the connector(s) are mechanically retained by the PCB and to provide a low-loss path between the contacts of the connectors and the corresponding mounting holes of the PCB.

By using a press-fit connection to connect the connector(s) to the PCB, it is not necessary for the connector(s) and cables to be compatible with solder reflow processes. Accordingly, a wide range of materials may be used to form the connector(s) and cables, including materials that are unsuitable for solder reflow processes. However, instead of a press-fit connection, the connector(s) may be attached to the PCB using other types of connections, including fusible connections, such as solder, for example. In addition, the connectors can use the same solder as the solder that is used to assemble the PCB. Specifically, the connectors may alternatively be attached to the PCB as surface-mount components. As shown in step 3, the cage is then press-fit to the PCB.

Furthermore, other components, such as heat sinks, may be added to the integrated PCB prior to, during, in between, or after any of the steps shown in FIG. 33.

The embodiments of the present invention described above can be compatible with the QSFP specifications. That is, a connector according to an embodiment of the present invention can be a female or card edge connector that is able to mate with a male or card connector, such as a QSFP-type of transceiver. However, a connector according to an embodiment of the present invention does not have to include connections to a substrate or PCB that comply with the QSFP specifications. According to the QSFP specifications, each of the contacts included in a female QSFP connector are directly connected to a corresponding pad on a substrate or PCB. The pads on the substrate or PCB are then connected to traces formed in the substrate or PCB. In contrast, according to an embodiment of the present invention, some of the contacts within a QSFP connector are directly mated to a substrate or PCB, while the remaining contacts are mated to shielded cables.

Accordingly, by transmitting certain signals, such as high-frequency signals, via shielded cables rather than via traces of a substrate or PCB, board-layout flexibility, high bandwidth, and low crosstalk are reliably achieved. Further, long routing paths to components mounted on a substrate or PCB, such as an IC, may be used, since a high degree of signal integrity is maintained by the use of shielded cables for the high-frequency signals.

For example, as compared with the overall data transfer rate of 40 Gbit/sec of conventional QSFP connectors, a QSFP connector according to an embodiment of the present invention provides overall data transfer rates of 100 Gbit/sec or more. Specifically, according to an embodiment of the present invention, data transfer rates of 28 Gbit/sec are able to be achieved in each of the four channels.

Furthermore, because high-frequency signals are transmitted through shielded cables rather than through traces in the substrate, it is not necessary for the substrate to be made of special materials. That is, because the dielectric properties of the substrate are not critical due to frequency signals being transmitted through shielded cables, the substrate may be made of standard PCB materials, such as FR-4, for example. Further, the substrate may be made of other materials, for example, Megtron™ from Panasonic Inc., Nelco™ from Park Electrochemical Corp., Rodgers™ from Sunstone Circuits Inc., and other suitable materials.

Specifically, the embodiments of the present invention can be configured to be used with the QSFP+28 specification to augment the SFF-8672 specification for Small Form Factor pluggable connector systems running at 28 Gbit/s. Embodiments of the present invention are also applicable to the other speed ratings including QSFP+14, QSFP+10, QSFP+, and QSFP-DD which are respectively defined by the SFF-8672, SFF-8682, SFF-8436, and QSFP-DD Hardware Specification for QSPF Double Density 8× Pluggable Transceiver, Rev. 5.0 specifications. These specifications represent a class of backward-compatible, module-plug connector systems, which provide increased performance with each subsequent generation. The embodiments of the present invention can be applied to any of these specifications and can be compatible with future higher speed specifications and applications.

In addition, the embodiments of the present invention are not limited to QSFP+ related specifications and systems, and can also be applied to similar pluggable-module systems, such as CXP and HD, which are respectively defined by the SFF-8647 and SFF-8644 specifications.

The cables may include various different wire gages for the conductors of the cables. However, the cables can have conductor gages between 24 AWG and 34 AWG. Cables with lower gauge conductors have less flexibility but lower transmission losses, while cables with higher gauge conductors have more flexibility but higher transmission losses. Accordingly, higher data transfer rate applications may benefit from use of lower gauge cables, since they have lower transmission losses. However, if lower data transfer rates are acceptable, higher gauge cables may be used to permit greater flexibility in IC placement and overall PCB layout.

The characteristic impedance of the cables is chosen to match those of the mating components, since matching impedances reduce unwanted reflections of high-frequency signals. The impedance values for the cables can be in the range of about 80Ω to about 100Ω, for example.

According to embodiments of the present invention, high-speed cables may be attached directly to an IC, instead of being connected to the IC through the PCB. An interconnect, other than through the PCB, may be included between the high speed cables and IC. The embodiments of the present invention can be applied to any system currently in use or being developed that requires high-bandwidth data transfer from a connector to an IC. According to embodiments of the present invention, integrated PCB assemblies may be used as line cards, mother boards, PCB controls, or other elements in digital electronic systems. The embodiments of the present invention can be used with many data transfer formats including, for example, InfiniBand, Gigabit Ethernet, Fibre Channel, SAS, PCIe, XAUI, XLAUI, XFI, and other suitable data transfer formats.

While embodiments of the present invention have been described above, it is to be understood that variations and modifications will be apparent to those skilled in the art without departing the scope and spirit of the present invention. The scope of the present invention, therefore, is to be determined solely by the following claims.

What is claimed is:

1. A connector comprising:

a housing;

a cage surrounding the housing;

first contacts that are located in the housing and that transmit high-speed signals;

second contacts that are located in the housing, that transmit low-speed signals, and that each include a portion that extends upward from an uppermost top surface of the housing;

first cables connected to the first contacts; and second cables connected to the second contacts.

2. The connector of claim 1, further comprising a control substrate; wherein the portion of each of the second contacts that extends upward from the uppermost top surface of the housing is connected to the control substrate; and the second cables are connected to the second contacts through the control substrate.

3. The connector of claim 1, wherein the second cables are crimped to the portion of each of the second contacts that extends upward from the uppermost top surface of the housing.

4. The connector of claim 1, further comprising wafers located within the housing; wherein the second contacts are included in the wafers.

5. The connector of claim 1, further comprising additional second contacts that are located in the housing, that transmit low-speed signals, that each include a portion that extends from a bottom surface of the housing, and that are not connected to any cables.

6. The connector of claim 1, further comprising additional first contacts that are located in the housing and that are connected to ground.

7. The connector of claim 6, wherein
the first cables include shields; and
the additional first contacts are connected to the shields.

8. The connector of claim 1, wherein each of the second contacts includes a right angle bend.

9. The connector of claim 1, wherein the connector is compatible with Quad Small Form-factor Pluggable (QSFP) specifications as defined in SFF-8672 specification, SFF-8672 specification, SFF-8682 specification, SFF-8436 specification, or QSFP-DD Hardware Specification for QSFP Double Density 8× Pluggable Transceiver (Rev. 5.0).

10. A connector system comprising:
a base substrate; and
the connector of claim 1 connected to a first surface of the base substrate.

11. The connector system of claim 10, further comprising an additional connector connected to a second surface of the base substrate opposite to the first surface; wherein
the additional connector includes:
a housing; and
a cage surrounding the housing.

12. The connector system of claim 11, wherein the additional connector is compatible with Quad Small Form-factor Pluggable (QSFP) specifications as defined in SFF-8672 specification, SFF-8672 specification, SFF-8682 specification, SFF-8436 specification, or QSFP-DD Hardware Specification for QSFP Double Density 8× Pluggable Transceiver (Rev. 5.0).

13. The connector of claim 1, wherein
the first contacts are configured to attach to a mounting substrate and define a mounting interface;
the uppermost top surface of the housing is positioned parallel to the mounting interface; and
second cables electrically connected to the second contacts.

14. A stacked connector comprising:
a first connector that includes first low-speed contacts and first high-speed contacts;
a second connector that is stacked on top of the first connector and that includes second low-speed contacts and second high-speed contacts, wherein each of the second low-speed contacts includes a portion that extends from an uppermost top surface of the second connector;
a cage surrounding the first connector and the second connector;
first high-speed cables connected to the first high-speed contacts;
second high-speed cables connected to the second high-speed contacts; and
low-speed cables connected to the second low-speed contacts.

15. The stacked connector of claim 14, further comprising a control substrate; wherein
the portion of each of the second low-speed contacts that extends from the uppermost top surface of the second connector are connected to the control substrate; and
the low-speed cables are connected to the second low-speed contacts through the control substrate.

16. The stacked connector of claim 14, wherein the low-speed cables are crimped to the portion of each of the second low-speed contacts that extends from the uppermost top surface of the second connector.

17. The stacked connector of claim 14, wherein the first connector further includes additional first low-speed contacts that each include a portion that extends from a bottom surface of the housing and that are not connected to any cables.

18. The stacked connector of claim 14, wherein the first low-speed contacts are connected to the low-speed cables.

19. The stacked connector of claim 14, further comprising a spacer between the first connector and the second connector.

20. The stacked connector of claim 14, wherein the first connector and the second connector are compatible with Quad Small Form-factor Pluggable (QSFP) specifications as defined in SFF-8672 specification, SFF-8672 specification, SFF-8682 specification, SFF-8436 specification, or QSFP-DD Hardware Specification for QSFP Double Density 8× Pluggable Transceiver (Rev. 5.0).

21. A stacked connector system comprising:
a base substrate; and
the stacked connector of claim 14 connected to the base substrate.

22. A connector system comprising:
a base substrate;
a first connector connected to a first surface of the base substrate and including:
a first housing including first contacts directly connected to the base substrate in a first area; and
a first cage surrounding the first housing; and
a second connector connected to a second surface of the base substrate opposite to the first surface and including:
a second housing including:
second contacts directly connected to the base substrate in a second area; and
additional second contacts that each include a portion that extends upward from an outermost surface of the second housing that is on an opposite side of the second housing as the base substrate; and
a second cage surrounding the second housing; wherein
when viewed in a plan view with respect to the base substrate, the first and second areas do not overlap.

23. The connector system of claim 22, wherein the first connector and the second connector are compatible with Quad Small Form-factor Pluggable (QSFP) specifications as defined in SFF-8672 specification, SFF-8672 specification, SFF-8682 specification, SFF-8436 specification, or QSFP-DD Hardware Specification for QSFP Double Density 8× Pluggable Transceiver (Rev. 5.0).

24. The connector system of claim 22, wherein a portion of the second cage does not overlap with the first cage in the plan view.

25. The connector system of claim 22, wherein the second connector further includes cables directly connected to the additional second contacts within the second housing.

26. The connector system of claim 22, wherein
the first area is defined by all contacts in the first housing directly contacting the base substrate, and
the second area is defined by all contacts in the second housing directly contacting the base substrate.

27. The connector system of claim 22, wherein
the first cage completely surrounds the first housing when viewed in plan, and
the second cage completely surrounds the second housing when viewed in plan.

28. The connector system of claim 22, wherein
the first cage completely surrounds the first contacts when viewed in plan, and
the second cage completely surrounds the second contacts when viewed in plan.

29. The connector system of claim 22, wherein
the first connector includes only surface mount contacts, and
the second connector includes only press-fit contacts directly connected to the base substrate.

* * * * *